United States Patent [19]

Masuda et al.

[11] 4,414,325

[45] Nov. 8, 1983

[54] METHOD FOR MEASUREMENT OF TRACE ENZYME

[75] Inventors: Nobuhito Masuda; Yuji Mihara; Masaki Okazaki; Hajime Makiuchi, all of Kanagawa, Japan

[73] Assignee: Fuji Photo Film Co., Ltd., Kanagawa, Japan

[21] Appl. No.: 298,814

[22] Filed: Sep. 2, 1981

[30] Foreign Application Priority Data

Sep. 2, 1980 [JP]  Japan ................... 55-120600

[51] Int. Cl.[3] ............ G01N 33/52; G01N 33/54; G01N 33/58
[52] U.S. Cl. ........................... 435/7; 430/537; 430/631; 435/4; 436/805
[58] Field of Search ............... 23/230 B, 915; 424/8, 424/12; 435/7, 4; 430/537, 631

[56] References Cited

U.S. PATENT DOCUMENTS

| | | | |
|---|---|---|---|
| 4,331,444 | 5/1982 | Mihara | 23/230 B |
| 4,337,063 | 6/1982 | Mihara | 23/230 B |
| 4,337,065 | 6/1982 | Hiratsuka | 23/230 B |

*Primary Examiner*—Sidney Marantz
*Attorney, Agent, or Firm*—Sughrue, Mion, Zinn, Macpeak and Seas

[57] ABSTRACT

The amount of enzyme is determined by reacting an enzyme to be measured with a synthetic substrate having at least one structure to be specifically contacted with the enzyme and at least one spectral sensitizer structure, bringing either the reaction product having the spectral sensitizer structure or the unreacted synthetic substrate into contact with a silver halide emulsion layer, exposing the same to light of a spectral sensitizing wavelength region corresponding to the spectral sensitizer structure, developing the silver halide, and then measuring the optical density of developed silver and/or colored dye.

10 Claims, No Drawings

METHOD FOR MEASUREMENT OF TRACE ENZYME

BACKGROUND OF THE INVENTION

1. Field of the Invention

This invention relates to a method for measurement of a trace enzyme, more particularly, to a method for photochemical measurement of a trace enzyme.

2. Development of the Invention

Various methods have heretofore been developed for measuring the activity of a trace enzyme. For example, there are: a turbidimetric method wherein the decrease in turbidity caused by an enzyme reaction is traced using a suspension of a high molecular weight substrate; an absorptiometric method wherein a high molecular weight substrate is decomposed or cleaved by an enzyme and, after precipitating and removing undecomposed substrate, soluble component is determined by an absorbance measurement; a method wherein a dye or fluorescent substance is previously bound to a high molecular weight substrate, an enzymatic reaction is effected to decrease the molecular weight of the dye or fluorescent substance, and the fractionated dye or fluorescent substance of lower molecular weight is measured; and a method of quantitative assay wherein, using a substrate which is designed to change in absorption spectrum, form a color or form a fluorescent substance, based on a splitting-off or change in a part of the substrate after an enzymatic reaction, the resulting absorbancy or fluorescent intensity is measured, etc. (*SEIKAGAKU JIKKEN KOZA* (lectures on Biochemical Experiments), vol. 5, subtitled "Study on Enzymes", edited by the Biochemical Association, Japan, published by Tokyo Kagaku Dojin, 1975).

Most of these methods, however, quantitatively determine an amount of enzyme on the order of $\mu g/ml$. Even utilizing a type of substrate releasing a fluorescent substance (e.g., derivatives of coumarin, umbelliferone, etc.), which is recognized to be most sensitive among these conventional methods, it is only possible to measure an enzyme quantity on the order of ng/ml.

Therefore, in activity measurements of trace enzymes labelled in accordance with enzyme immunoassay, the development of more stable and more highly sensitive enzyme activity measurement methods has been desired.

Further, since the enzymes as biocomponents in blood, body fluids, urine and in tissues in the living body such as various organs, the brain, etc. mostly are present in a very small quantity, except for certain enzymes (amylase, GOT, GPT, etc.) which exist in a large amount, such enzymes cannot be determined by conventional measurement methods. Therefore, radioimmunoassay (hereinafter merely "RIA") which is an immunological measurement method using a radioactive isotope has recently been introduced. The principle of RIA is described in, for example, Kumahara and Shizume, *RADIOIMMUNOASSAY, New Edition*, pages 3 to 10 (1977), published by Asakura Publishing Co., Ltd., *KISO SEIKAGAKU JIKKENHO* (Basic Biochemical Experiments) (6), Biochemial Assay (1967), published by Maruzen Co., Ltd., Tokyo, *METHODS IN ENZYMOLOGY*, edited by Sidney P. Colowick et al, vols. I, II, III, V and VII, published by Academic Press, New York and *The Enzyme*, vols. 3, 4 and 5, Paul D. Boyer et al (1971), published by Academic Press, New York.

However, RIA as a quantitative assay for enzymes has disadvantages such as: (1) since it is an immunoassay, there is the possibility that the activity of an enzyme—which is the functional characteristic of the enzyme—will not be actually reflected; (2) there is the possibility that analogous enzymes and precursors having a similar antigenic site might be included in analytical data; and (3) in the case where the enzyme to be measured, for example, such as an enzyme in an antigen or antibody labelled with the enzyme used for the enzyme immunoassay, is bound to another component but not present in the free state, it is difficult to prepare an antibody corresponding to the aforesaid labelled antigen or antibody and design for a method for measurement is practically difficult.

RIA has further disadvantages due to the use of radioisotopes. That is: (1) potential injury to the person dealing with radiation is a matter of concern; (2) special places and controls are required for storage and waste disposal of the radioactive substances used; (3) the amount of radiation from the radioisotope is reduced with the passage of time due to the half decay of the isotope; and (4) measurement of the count of radioactivity requires expensive devices.

The information obtained by measuring enzyme activity using a specific substrate under given reaction conditions (e.g., concentration of substrate, total volume, reaction pH, reaction temperature, reaction time, ionic strength, salts co-existant, etc.) is generally classified as follows:

(1) The sum of enzyme activities having a catalytic action on the structure of the substrate in the system; or (2) Under the condition of constant enzyme concentration, a degree of inactivation depending upon purity of an enzyme, the presence or absence of inhibitors, intensity of inhibition, denaturation, etc., i.e., measure of specific activity.

Finally, the purpose of measuring the activity of an enzyme as a component in the living body is frequently to obtain mainly information per (1) above and the purpose of activity measurements of enzyme-labelled materials exterior a living body is to obtain mainly information per (1) and (2) above. As is well known, in any case, specific enzyme activity can only be measured by selecting a substrate corresponding to enzyme specificity.

The term "specificity" referred to herein is art-recognized and defines selective reactivity between substances, e.g., of an enzyme with its corresponding substrate.

SUMMARY OF THE INVENTION

As a result of research on assays for a trace enzyme, we have discovered a method for measurement of enzyme activity having an extremely high sensitivity, by the use of the substrate specifically possessed by an enzyme and the spectral sensitization characteristics of a photographically active spectral sensitizer.

One object of this invention is therefore to provide a method for measurement of enzyme activity of an extremely high sensitivity by the use of the substrate specificity of an enzyme and the photochemically active spectral sensitizing dye or spectral sensitizer (these terms are interchangeably used in the specification).

Another object of this invention is to provide a novel method for measurement of enzyme activity in the measurement of the activity of a labelled enzyme at the measurement step in enzyme immunoassay.

The term "trace" used herein refers to a minute quantity, generally in the order of μg/ml or less, while not limited thereto.

The measurement method of this invention provide not only a very high sensitivity but also is effectively applied to the situation where an enzyme is in the form of a conjugate or complex thereof with other organic materials (e.g., polymers, latexes, microcapsules, membranes); bacteria; microorganisms; components in the living body (e.g., hormones, peptides, proteins, lipoproteins, sugar proteins, glucosides, lipids, etc.), toxic substances; drugs; antibiotics, etc.).

The method for measurement of enzyme activity or a quantity of an enzyme according to this method comprises:

using a synthetic substrate comprising at least one spectral sensitizer structure (B) which has an absorption region at a longer wavelength (preferably, longer than 500 nm) than the absorption wavelength region intrinsic to silver halide and which spectrally sensitizes silver halide grains by contact with (adsorption to) the silver halide grains and at least one structure (A) to be specifically contacted with the enzyme to be measured, bringing either the reaction product comprising spectral sensitizer structure (B) formed by the enzyme reaction or the unreacted synthetic substrate into contact with silver halide followed by development, and, measuring the amount of developed silver and/or the amount of colored dye obtained as an optical density.

The term "synthetic substrate" used herein refers to a substrate synthesized in the laboratory as opposed to subtrates derived from living tissues and is recognized in the art (see, e.g., Japanese Patent Application OPI 52691/77; in specification, OPI number used for identifying a Japanese patent application as a citation refers to an application laid open to public inspection while its examination has not yet been completed). The synthetic substrate used in this invention comprises structure (A) and structures (B) described above.

Structure (A) generally comprises a site to be catalytically affected with an enzyme to be measured (in other words, a site to be catalytically, e.g., cleaved with the enzyme) and a site to be specifically recognized with the enzyme (i.e., a recognition site or binding site) and thus specifically contacted with the enzyme.

The enzymatic reaction which occurs in the measurement method of this invention is illustratively shown below.

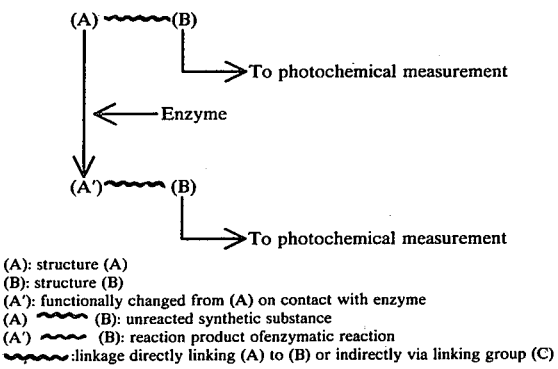

(A): structure (A)
(B): structure (B)
(A'): functionally changed from (A) on contact with enzyme
(A) ∼∼∼ (B): unreacted synthetic substance
(A') ∼∼∼ (B): reaction product of enzymatic reaction
∼∼∼∼:linkage directly linking (A) to (B) or indirectly via linking group (C)

One major feature of the combination of a spectral sensitizer and a silver halide, a prime feature of which is the detection means of this invention, is that sensitivity is very high and sensitivity can be controlled by controlling the amount of light used for exposure. Therefore, in the determination of an enzyme—even if the concentrational range can easily be covered by exposing plural spots of an enzyme sample under different exposure conditions and thereafter treating them simultaneously. For example, even if a testing sample containing an enzyme in a 10 times concentration that of an original concentration is exposed by a 1/10 exposure amount, the same optical density as given by the enzyme of an original concentration is achieved. Therefore, the enzyme reaction including the most complicated steps can be performed by one operation only using the original testing sample.

Thus, still another object of this invention is to provide a method of measuring at high sensitivity enzyme activity having a very wide measurement capability.

DESCRIPTION OF THE PREFERRED EMBODIMENTS

In the method of this invention, typically a synthetic substrate containing at least one structure (A) which is specifically contacted with an enzyme to be measured and at least one spectral sensitizing dye structure (B) are mixed and reacted with a testing sample containing the enzyme to be measured in an appropriate buffer solution, the formed reaction product containing the spectrally sensitizing dye structure (B) is separated from the unreacted synthetic substrate in the manner described hereinafter, and one of them is spotted on a layer containing silver halide. In this case, the reaction mixture may also be directly spotted onto a silver halide-containing sheet itself having a separation means such as a separation layer, etc.

Then, the silver halide-containing layer is exposed to light of the sensitizing wavelength for the spectral sensitizer used and then developed, and the optical density of developed silver and/or the colored dye at the spotted portions is measured, whereby the enzyme activity of the testing sample can be determined. Also when the value of the enzyme activity per amount of an enzyme (specific activity) is constant, the amount of the enzyme to be measured can be determined from the optical density of the developed silver or colored dye by reference to corresponding values on a calibration curve or, in the case of calibrating changes of specific activity, etc., the specific activity can be calculated using the same calibration curve and comparing to the black density and/or the colored dye density on the same enzyme quantity basis. This is because the optical density of the thus formed blackened areas and/or colored dye is proportional to the amount of spectral sensitizer adsorbed on silver halide, which is in turn proportional to the amount of the enzyme to be measured.

The method of this invention can apply not only to enzymes in the living body but also to enzymes, e.g., present in soil, culture solutions, culture media, etc., enzymes recovered from a living body or the aforesaid materials, enzymes immobilized to various soluble or insoluble carriers, and enzymes contained in the enzyme-labelled antigens or antibodies.

The object of this invention is to provide a measuring method and a determination method for enzyme activity of high sensitivity without using radioactive isotopes, which can be used not only for enzymes in a living body but also for enzymes existing in soil, culture solutions, culture media, etc.; enzymes recovered from a living body or the aforesaid materials; enzymes immobilized to various soluble or insoluble carriers; and enzymes used for labelling antigens or antibodies.

Spectral sensitizing dyes containing spectral sensitizing structure (B) in a synthetic substrate used in this invention have a property of imparting spectral sensitivity to silver halide. Such dyes are known as spectral sensitizing dyes for photographic materials and include, for example: cyanine dyes, merocyanine dyes, hemicyanine dyes, styryl dyes, etc. These dyes are specifically described in The Theory of the Photographic Process (4th edition), edited by T. H. James (1977), published by Macmillan Co., Ltc., *Cyanine Dyes and Related Compounds,* F. M. Hamer (1964), Interscience Publishers, etc.

In more detail, merocyanine dyes as described in U.S. Pat. Nos. 2,493,748, 2,519,001 and 2,652,330, German Pat. No. 1,177,481 and French Pat. No. 1,412,702, cyanine dyes as described in U.S. Pat. Nos. 2,238,213, 2,503,776, 2,537,880, 3,196,017 and 3,397,060, German Pat. Nos. 929,080, 1,028,718, 1,113,873, 1,163,671 and 1,177,482, French Pat. No. 1,359,683, British Pat. Nos. 840,223, 886,270, 886,271 and 904,332, Belgian Pat. No. 654,816 and Japanese Patent Publications Nos. 14112/65 and 23467/65 ("patent publication" used in specification means an application published for purpose of opposition and is available for public inspection), etc., are all effective dyes for this invention.

These dyes can also be employed in combinations of two or more thereof. For example, supersensitization including the use of dyes as described in Japanese Patent Publications Nos. 4932/68, 4936/68, 22884,68, etc. is also effective for this invention. Further, supersensitization as described in U.S. Pat. No. 2,947,630, 2,933,390, 2,937,089, 3,617,295 and 3,635,721, French Pat. No. 1,500,218, etc., is also effective. In this case, the supersensitizing dye combination can be mixed together with the labelled trace components, such as an antigen or antibody, or can be previously incorporated into silver halide emulsion.

Enzymes which are to be measured in accordance with this invention are known, depending upon mode of contact in enzyme reaction, as hydrolase type enzymes (e.g., protease, nuclease, glycogenase, esterase, lipase, etc.) which cleave bonds in substrate molecules, e.g., a peptide bond, ester bond, phosphate bond, glucoside bond, acid amide bond, etc., by the addition of a water molecule; so-called eliminase and transferase type enzymes which release a specific functional group contained in substrates or transfer it to other substrates; electron transfer type enzymes which contribute to the transfer of oxygen to the substrates; redox type enzymes which contribute to the redox reaction of the substrates, etc.

Representative examples of enzymes which are objectives to be assayed in accordance with the method of this invention include proteases such as trypsin, plasmin, kallikrein, thrombin, chymotrypsin, urokinase, catepsin, streptomyces alkali protease, papain, ficin, bromerain, renin, collagenase, erastase, etc.; peptidases such as leucine aminopeptidase, aminopeptidase, acylaminopepsidase, carboxypeptidase, dipeptidyl peptidase, etc.; nucleases e.g., ribonuclease A, ribonuclease $T_1$, deoxyribonuclease $A_1$, endonuclease, etc.; glycogenase including lyase type enzymes e.g., amylase, lysozyme, glucosidase, galactosidase, mannosidase, phosphorylase, glucanase, hyaluronidase, chondroitinase, arginic acid lyase, etc.; lipases, e.g., lipase, phospholipase, etc.; transferase, e.g., transcarbamylase, aminotransferase, acyltransferase, phosphotransferase, etc.; lyases, e.g., carboxylase, hydrolyase, ammonialyase, etc.

Such enzymes are described in detail, for example, in *ENZYME,* edited by Masaru Funatsu, published by Kodansha Publishing Co., Ltd., 1977, *DATABOOK OF BIOCHEMISTRY,* first & second separate volumes, edited by Biochemical Association, Japan, published by Tokyo Kagaku Dojin, 1979 & 1980, *The Enzyme,* vols. III, IV and V, Paul. D., Boyer et al., 1971, published by Academic Press, etc.

In the practice of the method of this invention, it is necessary for assaying the activity of an enzyme to react the synthetic substrate and the enzyme to be assayed and to bring either the reaction product containing the spectral sensitizer structure formed as a result of the enzyme reaction or the unreacted synthetic substrate into contact with a silver halide.

In the above-described enzyme reaction mode, either the reaction product formed by the enzyme reaction or the unreacted synthetic substrate can be detected since both the components differ from each other in chemical and physical properties. For example, both components can be separated from each other utilizing their difference in adsorptive property to silver halide or using another proper separation method (for example, ion exchange chromatography, high speed liquid chromatography, TLC, salting out, centrifugal separation, coprecipitation with a polymer, decantation, ultrafiltration, affinity chromatography, immune reaction, use of an adsorbent such as activated carbon, etc.). The method of this invention can be applied to any types of enzymes described above and details thereof are described in *DATABOOK OF BIOCHEMISTRY,* Chapter 10, second separate volume, edited by Biochemical Association, Japan, published by Tokyo Kagaku Dojin, 1979. Of these enzymes, hydrolase type enzymes can extremely easily be assayed in accordance with the method of this invention.

The method of this invention can be utilized for the activity measurement and determination of enzymes having the above described contact modes in the enzymes labelled to antigens of antibodies as are used in enzyme immunoassay. Enzyme immunoassay is a method of detecting and determining at high sensitivity trace components in the living body or trace drugs utilizing a specific binding mode of an antigen-antibody reaction and the catalytic action of enzymes in combination. In other words, in enzyme immunoassay, after binding an enzyme to an antigen or antibody, the extent of the antigen-antibody reaction is detected using the enzyme activity as a labelling substance and the amount of the antigen or antibody is determined based thereon. Such measurement systems are generally classified as follows: the case where the antigen and/or antibody is to be measured; the case where an enzyme-labelled antigen (or antibody) is competitive or not competitive with an enzyme-unlabelled antibody (or antigen), and the case where a labelled antigen (or antibody) is competitive with an unlabelled antibody (or antigen), the antigen-bound antibody is separated or not separated from the unbound antigen or antibody prior to measurement. Of these methods, typical methods include (1) a solid phase method, (2) a double antibody method, (3) a homogenous system enzyme immunoassay, and (4) a sandwich method. Details of these methods are described in, for example, Wisdom, *Clin. Chem.*, vol. 22, 1243 (1976). A. Voller et al. *The Enzyme Linked Immunosorbent Assay*, published by Flowing Publications, Guerney, Europe (1977); M. J. O'Sullivan et al. *Annals of Clinical Biochemistry*, vol. 16, 221 (1979), Kiyoshi Miyai, *Enzyme Immunoassay*, Clinical Test, vol. 22, No. 11, extra edition in 1978, and Eiji Ishikawa, Tadashi Kawai and Kiyoshi Miyai, *KOSO MENEKI SOKUTEIHO (Enzyme Immunosssay)*, published by Igaku Shoin, 1978.

By the application of the method of this invention for activity measurement of an enzyme labelled to an antigen or antibody, the enzyme activity can be assayed at higher sensitivity and with greater safety than with conventional methods, whereby the sensitivity and the accuracy of the immunoassay is enhanced.

Structure (A) used in this invention which is specifically contacted with an enzyme to be measured, generally comprises a contact site for an enzyme, such as a peptide bond (acid amide bond), an ester bond, a phosphate bond or a glucoside bond to hydrolase enzymes, an amino group, a carboxy group, etc. to transferase enzymes; and a recognition site or binding site for the enzyme such as an amino acid residue, sugar, a nucleic acid base, etc. These are more specifically described in, for example, *DATABOOK OF BIOCHEMISTRY*, first and second separate volumes, edited by Biochemical Association, Japan, published by Tokyo Kagaku Dojin, 1979 & 1980, and *The Enzyme*, vols III, IV and V, edited by Paul D., Boyer, et al, published by Academic Press, 1971, as substrate structures corresponding to the substrate specificity of an enzyme.

The synthetic substrate used in this invention is composed of at least one of the above described structures (A) corresponding to the substrate specificity of an enzyme and at least one of the above described spectral sensitizer structures (B), which are linked with each other directly or through linking group (C). At the conditions for linking these structures with each other: (1) the enzyme reactivity should not be inhibited by the linking; and (2) the spectrally sensitizing activity should not be lost by the linking.

Linking group (C) contains at least two functional groups in the molecule thereof which are capable of linking (A) and (B) and is exemplified by a group derived from an amino acid (e.g., —NH—CH(R)—CO wherein R is an alkyl group which may be substituted), peptide, polyamino acid, monosaccharide, disaccharide, polysaccharide (oligomer and polymer), nucleic acid base, nucleotide, nucleoside, polynucleoside, polynucleotide, etc. The linking is effected via functional groups on structure (A) (e.g., an amino group, an imino group, a carboxy group, a hydroxy group, a sulfhydryl group, or a group capable of reacting with these groups) and functional groups on spectral sensitizer structure (B) (e.g., an amino group, an imino group, a carboxy group, a hydroxy group, a sulfhydryl group, or a group capable of reacting with these groups, etc.). These functional groups may exist in each structure or may be introduced into each structure by the chemical reaction therewith of a compound containing such a group. Further, these functional groups may be employed singly or in combination.

In general, most substrates contain functional groups such as an amino group(s), a carboxy group(s), a hydroxy group(s), etc., therein. For example, in proteolytic enzymes their substrates typically contain a hydroxy group(s) in the molecule thereof as a functional group(s) for effecting linking with a spectral sensitizer for introducing structure (B) or for effecting such a linking via linking group (C).

On the other hands, as the compound having a group capable of reacting with the aforesaid functional groups, there are the following compounds: alkyl chloroformates (e.g., diethyl chloroformate, isobutyl chloroformate, etc.), aldehydes (e.g., formaldehyde, glutaraldehyde, etc.), isocyanates (e.g., xylylene diisocyanate, tolylene diisocyanate, hexamethylene diisocyanate, etc.), thioisocyanates (e.g., xylylene thioisocyanate, etc.), vinyl compounds (e.g., divinyl ketone, methylene bisacrylamide, divinyl sulfone, etc.), active halides (e.g., cyanuric chloride, mucohalogenic acids, nitrophenyl chloride, phenol-2,4-disulfonyl chloride, etc.), active esters (e.g., p-toluenesulfonic acid succinyl ester, etc.), imidazolic acid amides (e.g., carbonyl diimidazole, sulfonyl diimidazole, trimidazolyl phosphate, etc.), pyridinium compounds (e.g., N-carbamoyl pyridinium, N-carbamoyloxypyridinium, etc.), sulfonic acid esters (e.g., alkanesulfonic acid esters, etc.), bismaleimides (e.g., N,N'-(1,3-phenylene)bismaleimide, etc.), diazonium compounds (e.g., bisdiazobenzidine, etc.), epoxy compounds (e.g., bisoxirane, etc.), acid anhydrides, carboxylic acids, ethyleneimines, etc.

For further linking structure (A) and structure (B) directly or through linking group (C), for example, a carboxy group amoung the aforesaid functional groups of the one structure moiety is activated in a conventional manner by a carbodiimide (e.g., 1-ethyl-3-(3-dimethylaminopropyl)carbodiimide, 1-cyclohexyl-3-(2-morphodinyl-4-ethyl)carbodiimide, N,N'-dicyclohexylcarbodiimide, etc.), an isoxazolium, a pseudo base, an active ester (e.g., benzenesulfonic acid hydroxysuccinimide ester, etc.), an alkyl chloroformate (e.g., isobutyl chloroformate, etc.), etc., and then a linking may be formed between the structure moiety having the activated carboxy group and the other structure moiety having a functional group, e.g., an amino group. Consequently, a peptide bond is formed.

With respect to the manner of a linking made between the functional group of structure (A) having specificity for an enzyme and the functional group of spectral sensitizer structure (B) or between each of the functional groups and the functional group of linking group (C), there are:

(1) linking by direct reaction of the functional groups with each other, (2) cross-linking by a compound having two or more active functional groups, and (3) linking formed by activating one of these functional groups using an activator and introducing the activated group to the other functional group (e.g., an amino group, a sulfhydryl group, etc.).

In the case of using linking group (C) in the reaction of linking the two functional moieties (structure (A) and structure (B)) in this invention, it is preferred that the reaction be performed successively from one side to the other in such a manner that structure (A) is linked to linking group (C) between a functional group on structure (A) and one functional group of linking group (C), and then another functional group of linking group (C) is bonded to a functional group on structure (B).

It is preferred that the respective linking reactions be performed in a molar ratio of the two components in the range of from 1/20 to 20/1, preferably from 1.5 to 5/1, more preferably from ½ to 2/1. That is, the molar ratio range applies to a) the linking of structure (A) and structure (A) and structure (B), b) the linking of structure (A) and linking group (C) and c) the linking of structure (B) and linking group (C).

The reactive groups and the reaction methods are described in detail in, e.g., *SEIKAGAKU JIKKEN KOZA* (Lectures on Biochemical Experiments), vol. 1, entitled "Chemistry of Proteins", vol. 2, entitled "Chemistry of Nucleic Acids", vol. 3 entitled "Chemistry of Lipids" and vol. 4, entitled "Chemistry of Glucoside", all edited by Biochemical Association, Japan, published by Tokyo Kagaku Dojin, 1976; and *PEPTIDE SYNTHESIS*, by Izumiya et al, published by Maruzen Publishing Co., Ltd., 1975, J. P. Greenstein et al, *CHEMISTRY OF THE AMINO ACIDS*, vols. I–III, 1961, John Wiley & Sons, Inc., New York, G. E. Mees et al, *CHEMICAL MODIFICATION OF PROTEINS*, 1971, Holden-Day Inc., San Francisco, etc.

As the spectrally sensitizing dye comprising the synthetic substrate used for measuring the activity of an enzyme in this invention, there are the above described spectrally sensitizing dyes, such as, for example, cyanine dyes, merocyanine dyes, hemicyanine dyes, etc., and it is preferred that such dyes have a structure capable of being introduced as structure (B) by a chemical reaction. Examples of particularly preferred dyes of the aforesaid dyes in this invention are shown below.

(1) Cyanine dyes of formula (I) having at least one mercapto, amino, hydroxy or carboxy group:

thiazole, 5-chlorobenzothiazole, 6-chlorobenzothiazole, 7-chlorobenzothiazole, 5-nitrobenzothiazole, 6-nitrobenzothiazole, 4-methylbenzothiazole, 5-methylbenzothiazole, 6-methylbenzothiazole, 5-bromobenzothiazole, 6-bromobenzothiazole, 5-iodobenzothiazole, 5-phenylbenzothiazole, 5-methoxybenzothiazole, 6-methoxybenzothiazole, 5-ethoxybenzothiazole, 5-ethoxycarbonylbenzothiazole, 5-phenethylbenzothiazole, 5-fluorobenzothiazole, 5-chloro-6-nitrobenzothiazole, 5-trifluoromethylbenzothiazole, 5,6-dimethylbenzothiazole, 5-hydroxy-6-methylbenzothiazole, tetrahydrobenzothiazole, 4-phenylbenzothiazole, 5-phenylbenzothiazole, naphtho(2,1-d)thiazole, naphtho(2,3-d)thiazole, 5-methoxynaphtho(1,2-d)thiazole, 7-ethoxynaphtho(2,1-d)thiazole, 8-methoxynaphtho(2,1-d)thiazole, oxazole, 4-methyloxazole, 4-nitrooxazole, 5-methyloxazole, 4-phenyloxazole, 4,5-diphenyloxazole, 4-ethyloxazole, benzoxazole, 5-chlorobenzoxazole, 5-methylbenzoxazole, 5-bromobenzoxazole, 5-fluorobenzoxazole, 5-phenylbenzoxazole, 5-methoxybenzoxazole, 5-nitrobenzoxazole, 5-trifluorobenzoxazole, 5-hydroxybenzoxazole, 6-methylbenzoxazole, 6-chlorobenzoxazole, 6-nitrobenzoxazole, 6-methoxybenzoxazole, 6-hydroxybenzoxazole, 5,6-dimethylbenzoxazole, 4,6-dimethylbenzoxazole, 5-ethoxybenzoxazole, naphtho(2,1-d)oxazole, naphtho(1,2-d)oxazole, naphtho(2,3-d)-oxazole, 5-nitronaphtho(2,1-d)oxazole, 4-methylselenazole, 4-nitroselenazole, 4-

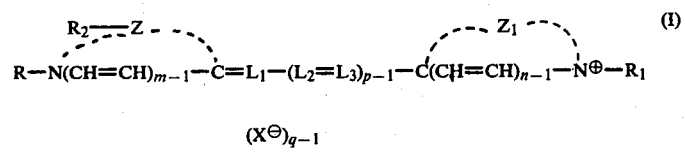

wherein m and n each represents 1 or 2 and may be the same or different; p represents 2 or 3; q represents 1 or 2; $L_1$, $L_2$ and $L_3$, which each may be the same or different represents a methine group optionally substituted with a lower alkyl group, an aryl group or a halogen atom; Z and $Z_1$, which may be the same or different, each represents the non-metallic atomic group necessary to complete a 5- or 6-membered nitrogen-containing heterocyclic nucleus; X represents an inorganic or organic anion; R and $R_1$, which may be the same or different, each represents an alkyl group having 1 to 18 carbon atoms, preferably 1 to 7 carbon atoms, optionally substituted with an aromatic group, an OH group, a sulfo group, etc.; and the cyanine dye forms a betaine type structure when qa is 1; $R_2$ is a substituent on Z and represents the carboxy-containing substituent of formula: $-P_i-Q_j-COOH$ (X), wherein P represents

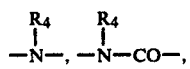

—CO—, —O— or —S—, where $R_4$ is a hydrogen atom, an alkyl group having 1 to 8 carbon atoms or a substituted alkyl group, Q represents an alkylene group, a substituted alkylene group, an arylene group, a substituted arylene group, an aralkylene group, an alkarylene group, a dipeptide residue or a tripeptide residue, i and j each is 0 or 1, and i and i may be the same or different.

Examples of nitrogen-containing heterocyclic nucleus represented by Z and $Z_1$ include thiazole, 4-methylthiazole, 4-phenylthiazole, 4,5-dimethylthiazole, 4,5-diphenylthiazole, benzothiazole, 4-chlorobenzonitroselenazole, 4-phenylselenazole, benzoselenazole, 5-chlorobenzoselenazole, 5-nitrobenzoselenazole, 5-methoxybenzoselenazole, 5-methoxybenzoselenazole, 5-hydroxybenzoselenazole, 6-nitrobenzoselenazole, 5-chloro-6-nitrobenzoselenazole, naphtho(2,1-d)selenazole, naphtho(1,2-d)selenazole, a 1-alkylimidazole, a 1-alkyl-4-phenylimidazole, a 1-alkylbenzimidazole, a 1-alkyl-5-chlorobenzimidazole, a 1-alkyl-5,6-dichlorobenzimidazole, a 1-alkyl-5-methoxybenzimidazole, a 1-alkyl-5-cyanobenzimidazole, a 1-alkyl-5-fluorobenzimidazole, a 1-alkyl-5-trifluoromethylbenzimidazole, a 1-alkylnaphthao(1,2-d)imidazole, a 1-aryl-5-chlorobenzimidazole, a 1-arylimidazole, a 1-arylbenzimidazole, a 1-aryl-5-chlorobenzimidazole, a 1-aryl-5,6-dichlorobenzimidazole, a 1-aryl-5-methoxybenzimidazole, a 1-aryl-5-cyanobenzimidazole, a 1-arylnaphtho(1,2-d)imidazole; wherein any alkyl group mentioned preferably being an unsubstituted alkyl group having 1 to 8 carbon atoms, such as a methyl group, ethyl group, propyl group, isopropyl group, butyl group, etc., or such an alkyl group hydroxy-substituted such as a 2-hydroxyalkyl, 3-hydroxyalkyl group, etc., any aryl group being preferably a phenyl group, halogen-substituted phenyl group (e.g., chloro-substituted phenyl group), alkyl-substituted phenyl group (e.g., methyl-substituted phenyl group), alkoxy-substituted phenyl group (e.g., methoxy-substituted phenyl group), etc.; a pyridine nucleus (e.g., 2-pyridine, 4-pyridine, 5-methyl-2-pyridine, 3-methyl-4-pyridine, etc.), a quinoline nucleus (e.g., 2-quinoline, 3-methyl-2-quinoline, 5-ethyl-2-quinoline, 6-methyl-2-quinoline, 6-nitro-2-quinoline, 6-amino-2-quinoline, 6-amino-2- quinoline, 8-fluoro-2-quinoline, 6-methoxy-2-quinoline, 6-mercapto-2-quinoline, 8-chloro-2-quinoline, 4-quinoline, 6-ethoxy-4-quinoline, 6-nitro-4-quinoline, 6-amino-4-quinoline, 8-chloro-4-quinoline, 8-fluoro-4-quinoline, 8-methyl-4-quinoline, 8-methoxy-4-quinoline, isoquinoline, 6-nitro-1-isoquinoline, 6-amino-1-isoquinoline, 3,4-dihydro-1-isoquinoline, 6-nitro-3-isoquinoline, etc.), an imidazo[4,5-b]quinoxaline nucleus (e.g., 1,3-diethylimidazo[4,5-b]quinoxaline, 6-chloro-1,3-diallylimidazo[4,5-b]quinoxaline, etc.), an oxadiazole nucleus, a thiadiazole nucleus, a tetrazole nucleus, a pyrimidine nucleus, etc.

Preferred examples of R or $R_1$ include methyl, ethyl, propyl, isopropyl, butyl, isobutyl, hexyl, octyl, dodecyl, octadecyl, etc. for an unsubstituted alkyl group; benzyl, β-phenethyl, etc. for an aralkyl group; 2-hydroxyethyl, 3-hydroxyethyl, etc. for a hydroxyalkyl group; 2-methoxyethyl, 2-(2-methoxyethoxy)ethyl, etc. for an alkoxyalkyl group; 2-carboxyethyl, 3-carboxypropyl, 4-carboxybutyl, etc.; 2-sulfoethyl, 3-sulfopropyl, 3-sulfobutyl, 4-sulfobutyl, 2-[3-sulfopropoxy]ethyl, 2-hydroxy-3-sulfopropyl, 3-sulfopropoxyethoxyethyl, etc. for a sulfo-substituted alkyl group; 3-sulfatopropyl, 4-sulfatobutyl, etc. for a sulfato-alkyl group; phenyl, naphthyl, methoxyphenyl, chlorophenyl, etc. for an aryl group; 2-(pyrrolidin-2-on-1-yl)ethyl, tetrahydrofurfuryl, etc. for a heterocyclic ring-substituted alkyl group; 2-acetoxyethyl, carboxymethoxymethyl, 2-methanesulfonylaminoethyl, etc.

When q is 1, the dye forms a betaine type structure.

Q in formula (X) is preferably an alkylene group having 1 to 10 carbon atoms, a substituted alkylene group or formula $$-\underset{R_{30}}{\underset{|}{CH}}-$$

wherein $R_{30}$ represents methyl, ethyl, propyl, isopropyl, isobutyl, t-butyl, hydroxymethyl, 1-hydroxyethyl, mercaptomethyl, 2-methylthioethyl, benzyl, β-hydroxybenzyl, 3-indolylmethyl, etc.), an arylene group (e.g., phenylene, etc.), a substituted arylene group (e.g., a substituted phenylene group), an aralkylene group, an alkarylene group, a dipeptide residue, or a tripeptide residue.

At least one of R, $R_1$, $R_2$ and $Z_1$ contains at least one of a mercapto, amino, hydroxy and carboxy group (hereafter, these groups are sometimes referred to as "carboxy, etc.-containing group), preferably at least one carboxy group (hereafter this group is sometimes referred to as "carboxy-containing group).

In particularly preferred dyes among the aforesaid dyes, only $R_2$ contains a carboxy group and typical examples of such $R_2$ groups are:

—COOH, —CH$_2$COOH, —(CH$_2$)$_2$COOH,

—NH—CH$_2$—COOH, —NH—CH$_2$CH$_2$COOH,

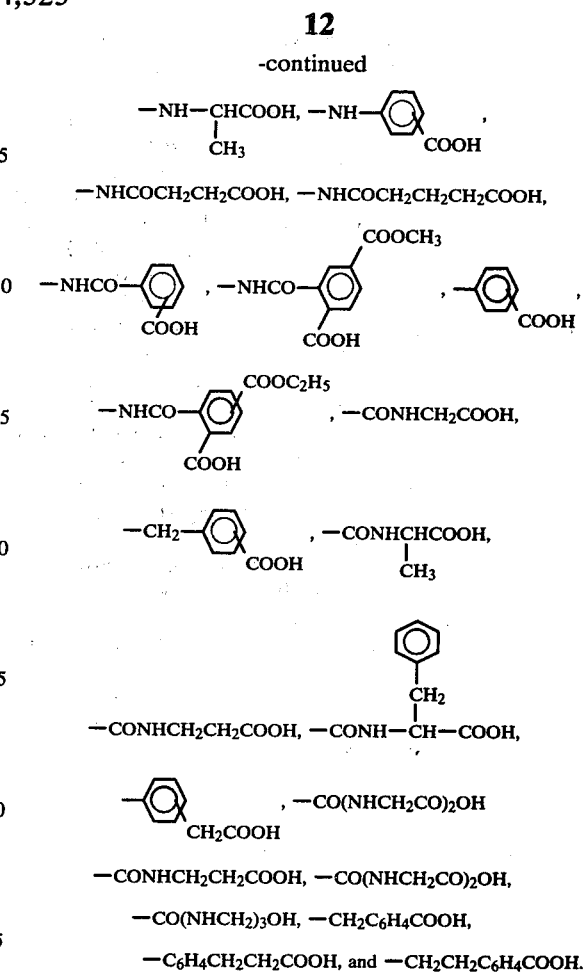

—CONHCH$_2$CH$_2$COOH, —CO(NHCH$_2$CO)$_2$OH,

—CO(NHCH$_2$)$_3$OH, —CH$_2$C$_6$H$_4$COOH,

—C$_6$H$_4$CH$_2$CH$_2$COOH, and —CH$_2$CH$_2$C$_6$H$_4$COOH.

Also, Z and $Z_1$ when only $R_2$ is the carboxy-containing group, preferably represent the above described thiazole nucleus (provided that in the case, as a matter of course, where N present on the cyanine chromophore of the terminal heterocyclic ring has the carboxy, etc.- or carboxy-containing group as a substituent, i.e., the case where R and $R_1$ are a carboxy, etc.- or carboxy containing group; hereafter the same), naphthothiazole nucleus, oxazole nucleus, benzoxazole nucleus, naphthoxazole nucleus, benzoselenazole nucleus, naphthoselenazole nucleus, imidazole nucleus, pyridine nucleus or quinoline nucleus.

Spectrally sensitizing dyes wherein only $R_2$ is carboxy-containing group are excellent in both solubility and reactivity and hence the use of such spectrally sensitizing dyes permits enzyme labelling at high efficiency.

(2) Merocyanine dyes of formula (II) below having at least one mercapto, amino, hydroxy or carboxy group on the heterocyclic ring:

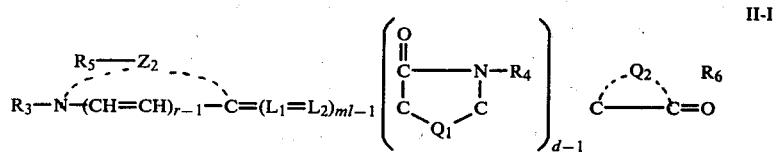

II-I wherein $Z_2$ has the same meaning as Z and $Z_1$;

$R_3$ and $R_4$ have the same meanings as R and $R_1$; $R_5$ and $R_6$ have the same meaning as $R_2$; r has the same meaning as n; $L_1$ and $L_2$ are as defined above;

$m_1$ represents 2, 3 or 4;

d represents 1, 2 or 3;

$Q_1$ represents an oxygen atom, a sulfur atom or —N—$R_6$ ($R_6$ represents an aliphatic group);

$Q_2$ represents a non-metallic atomic group necessary for completing a 5-membered or 6-membered nitrogen-containing heterocyclic nucleus; examples of such heterocyclic nuclei include:

a 2-pyrazolin-2-one nucleus (e.g., 3-methyl-1-phenyl-2-pyrazolin-5-one nucleus, 1-phenyl-2-pyrazolin-5-one nucleus, 1-(4-aminophenyl)-2-pyrazoline nucleus, 1-(2-benzothiazolyl)-3-methyl-2-pyrazolin-5-one nucleus, 1-phenyl-3-(2-sulfopropyl)-2-pyrazolin-5-one nucleus, 1-(4-sulfophenyl)-2-pyrazolin-5-one nucleus, 3-methyl-1-(4-carboxyphenyl-2-pyrazolin-5-one nucleus, 1-(4-carboxyphenyl)-2-pyrazolin-5-one nucleus, 1-(5-carboxybenzothiazol-5-one nucleus, 1-(5-carboxybenzothiazol-2-yl)-3-methyl-2-pyrazolin-5-one nucleus, etc.);

an isooxazolone nucleus (e.g., 3-(4-sulfonyl)-5-(4H)-isooxazolone nucleus, 3-(4-sulfobutyl)-5(4H)-isoxazolone nucleus, 3-(4-carboxyphenyl)-5-(4H)-isooxazolone nucleus, 3-(2-carboxyethyl)-5-(4H)-isooxazolone nucleus, etc.);

an oxindol nucleus (e.g., 1-ethyl-2,3-dihydro-2-oxindol nucleus, 1-sulfoalkyl-2,3-dihydro-2-oxindol nucleus, etc.,);

a barbituric acid nucleus or 2-thiobarbituric acid nucleus {such as barbituric acids or thiobarbituric acids containing, for example, a 1-alkyl (e.g., 1-methyl, 1-ethyl, 1-propyl, 1-heptyl, etc.,), a 1,3-dialkyl (e.g., 1,3-dimethyl, 1,3-diethyl, 1,3-dipropyl, 1,3-diisopropyl, 1,3-dicyclohexyl, 1,3-di($\beta$-methoxyethyl), etc.,), a 1,3-diaryl (e.g., 1,3-diphenyl, 1,3-di(p-chlorophenyl), 1,3-di(p-ethoxycarbonylphenyl), etc.,), a 1-sulfoalkyl (e.g., 1-(2-sulfoethyl), 1-(3-sulfopropyl), 1-(4-sulfoethyl), etc.,), a 1,3-disulfoalkyl (e.g., 1,3-di(2-sulfoethyl), 1,3-di(3-sulfopropyl), 1,3-di(4-sulfocyclohexyl), etc.), a 1-sulfoaryl (e.g., 1-(4-sulfophenyl), etc.,), a 1-(4-carboxyphenyl), a 1-carboxymethyl, etc.} group;

a rhodanine nucleus (e.g., a rhodanine nucleus, a 3-sulfoalkylrhodanine nucleus (e.g., 3-(2-sulfoethyl)rhodanine nucleus, 3-(3-sulfopropyl)rhodanine nucleus, 3-(4-sulfobutyl)rhodanine nucleus, etc.,), a 3-sulfoarylrhodanine nucleus (e.g., 3-(4-sulfophenyl)rhodanine nucleus, etc.,), a 3-alkylrhodanine nucleus (e.g., 3-ethylrhodanine nucleus, 3-allylrhodanine nucleus, etc.,), a 3-carboxyalkylrhodanine nucleus (e.g., 3-carboxymethylrhodanine nucleus, 3-(2-carboxyethyl)rhodanine nucleus, 3-(4-carboxybutyl)rhodanine nucleus, etc.,), a 3-arylrhodanine nucleus (e.g., 3-phenylrhodanine nucleus, 3-(4-carboxyphenyl)rhodanine nucleus, 3-[4-(2-aminoethylenecarbamoylphenyl]rhodanine nucleus, etc.);

a 2-thio-2,4-oxazolidinedione nucleus (e.g., 3-(2-sulfoethyl)-2-thio-2,4-oxazolidinedione nucleus, 3-(4-sulfobutyl)-2-thio-2,4-oxazolidinedione nucleus, 3-ethyl-2-thio-2,4-oxazolidinedione nucleus, 3-(3-carboxypropyl)-2-thio-2,4-oxazolidinedione nucleus, etc.);

a thiazolidinedione nucleus (e.g., 3-(4-sulfophenyl)-2,4-thiazolidinedione nucleus, 3-(1-carboxyphenyl)-2,4-thiazolidinedione nucleus, 2,4-thiazolidinedione nucleus, 3-ethyl-2,4-thiazoldinedione nucleus, 3-phenyl-2,4-thiazolidinedione nucleus, 3-$\alpha$-naphthyl-2,4-thiazolidinedione nucleus, etc.);

a thiazolidinone nucleus (e.g., 3-(2-sulfoethyl)-4-thiazolidinone nucleus, 3-(4-sulfophenyl)-4-thiazolidinone nucleus, 3-(4-carboxyphenyl)-4-thiazolidinone nucleus, etc.,);

a 2,4-imidazolidinedione (hydrantoin) nucleus (e.g., 3-(2-sulfoethyl)-2,4-imidazolidinedione nucleus, 3-(4-sulfophenyl)-2,4-imidazolidinedione nucleus, 3-ethyl-2,4-imidazolidinedione nucleus, 3-phenyl-2,4-imidazolidinedione nucleus, 1,3-diethyl-2,4-imidazolidinedione nucleus, 1-ethyl-3-phenyl-2,4-imidazolidinedione nucleus, 1-ethyl-3-phenyl-2,4-imidazolidinedione nucleus, 1,3-diphenyl-2,4-imidazolidinedione nucleus, 3-carboxymethyl-2,4-imidazolidinedione nucleus, 3-(2-carboxyethyl)-2,4-imidazolidinedione nucleus, 3-(4-carboxyphenyl)-2,4-imidazolidinedione nucleus, 3-[4-(2-aminoethylene)carbamoylphenyl]-2,4-imidazolidinedione nucleus, etc.);

a 2-thio-2,4-imidazolidinedione nucleus (i.e., a 2-thiohydantoin nucleus) (e.g., 2-thio-2,4-imidazolidinedione nucleus, 3-(4-sulfobutyl)-2-thio-2,4-imidazolidinedione nucleus, 3-carboxymethyl-2-thio-2,4-imidazolidinedione nucleus, 3-(2-carboxyethyl)-2-thio-2,4-imidezolidinedione nucleus, 3-phenyl-2-thio-2,4-imidazolidinedione nucleus, 3-(3-sulfopropyl)-2-thio-2,4-imidazolidinedione nucleus, 1,3-diethyl-2-thio-2,4-imidazolidinedione nucleus, 1-ethyl-3-phenyl-2-thio-2,4-imidazolidinedione nucleus, 1,3-diphenyl-2-thio-2,4-imidazolidinedione nucleus, 3-(4-carboxyphenyl)-2-thio-2,4-imidazolidinedione nucleus, 3-(4-carboxyphenyl)-1-ethyl-2-thio-2,4-imidazolidinedione nucleus, 3-[4-(2-aminoethylene)carbamoylphenyl]-1-ethyl-2-thio-2,4-imidazolidinedione nucleus, etc.), and a 2-imidazolin-5-one nucleus (e.g., 2-(3-sulfopropyl)-2-imidazolin-5-one nucleus, 2-carboxymethyl-2-imidazolin-5-one nucleus, etc.,).

As described above, the heterocyclic ring has at least one carboxy etc.-containing group. In other words, at least one of $R_3$, $R_4$, $R_5$, $Q_1$ and $Q_2$ contains at least one group selected from a mercapto group, an amino group, a hydroxy group, and a carboxy group, preferably at least one carboxy group.

Preferred examples of the carboxy-containing groups are the same as given for $R_2$ in formula (I) above.

These carboxy-containing groups are also typical examples of carboxy-containing groups in following formulae III and IV.

(3) Rhodacyanine dyes of formula (III) below, wherein a group containing at least one mercapto, amino, hydroxy or carboxy group is present:

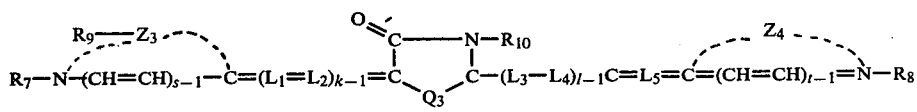

wherein $Z_3$ and $Z_4$ have the same meaning as Z and $Z_1$ described above; $R_7$ and $R_8$ have the same meaning as R and $R_1$ described above; and $R_9$ has the same meaning as $R_2$ described above. Therefore, at least one of $R_7$, $R_8$, $R_9$, $R_{10}$, and $Q_3$ contains at least one group selected from a mercapto groups, an amino group, a hydroxy group, and a carboxy group, preferably at least one carboxy group.

Also, l and t have the same meaning as m and n described above and $L_1$ and $L_5$ have the same meaning defined above. $R_{10}$ has the same meaning as $L_1$, $L_2$ and $L_3$ as $R_4$; $Q_3$ has the same significance as $Q_1$; and k and l, which may be the same or different, each represents 1, 2, or 3.

(4) Merocyanine dyes of following formula II—II having the carboxy-containing group at the acid nucleus (these dyes correspond to the merocyanine dyes of above-described formula II-I wherein d is 1 and $=(L_1-L_2)_{m1-1}$ is $=(CH-CH)_{p-1}$):

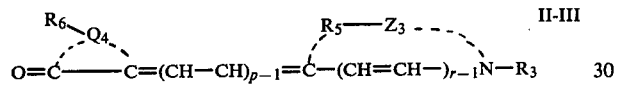

wherein
r has the same meaning as n defined above, and p represents 2 or 3; only $R_6$ of $R_3$, $R_5$ and $R_6$ has the carboxy-containing group.

$Z_3$ represents the non-metallic atomic group necessary for completing a 5-membered or 6-membered nitrogen-containing heterocyclic nucleus.

Examples of the heterocyclic nucleus are:
a thiazole nucleus (same as those illustrated relative to general formula I);
a benzothiazole nucleus (e.g., benzothiazole nucleus, 4-chlorobenzothiazole nucleus, 5-chlorobenzothiazole nucleus, 6-chlorobenzothiazole nucleus, 7-chlorobenzothiazole nucleus, 5-nitrobenzothiazole nucleus, 6-nitrobenzothiazole nucleus, 4-methylbenzothiazole nucleus, 5-methylbenzothiazole nucleus, 6-methylbenzothiazole nucleus, 5-bromobenzothiazole nucleus, 6-bromobenzothiazole nucleus, 5-iodobenzothiazole nucleus, 5-phenylbenzothiazole nucleus, 5-methoxybenzothiazole nucleus, 6-methoxybenzothiazole nucleus, 5-ethoxybenzothiazole nucleus, 5-carboxybenzothiazole nucleus, 5-ethoxycarbonylbenzothiazole nucleus, 5-phenethylbenzothiazole nucleus, 5-fluorobenzothiazole nucleus, 5-chloro-6-nitrobenzothiazole nucleus, 5-trifluoromethylbenzothiazole nucleus, 5,6-dimethylbenzothiazole nucleus, 5-hydroxy-6-methylbenzothiazole nucleus, tetrahydrobenzothiazole nucleus, 4-phenylbenzothiazole nucleus, 5-phenylbenzothiazole nucleus, etc.);
a naphthothiazole nucleus (same as the naphthothiazole nuclei illustrated relative to formula I);
a thiazoline nucleus (e.g., thiazoline nucleus, 4-methylthiazoline nucleus, 4-nitrothiazoline nucleus, etc.);
an oxazole nucleus (same as the oxazole nuclei illustrated relative to formula I);

a benzoxazole nucleus (e.g., benzoxazole nucleus, 5-chlorobnenzoxazole nucleus, 5-methylbenzoxazole nucleus, 5-bromobenzoxazole nucleus, 5-fluorobenzoxazole nucleus, 5-phenylbenzoxazole nucleus, 5-methoxybenzoxazole nucleus, 5-nitrobenzoxazole nucleus, 5-trifluorobenzoxazole nucleus, 5-hydroxybenzoxazole nucleus, 5-carboxybenzoxazole nucleus, 6-methylbenzoxazole nucleus, 6-chlorobenzoxazole nucleus, 6-methoxybenzoxazole nucleus, 6-hydroxybenzoxazole nucleus, 4,6-dimethylbenzoxazole nucleus, 5-ethoxybenzoxazole nucleus, etc.);
a naphthoxazole nucelus (same as the naphthoxazole nucleis illustrated relative to formula I);
an oxazoline nucleus (e.g., 4,4-dimethyloxazoline nucleus, etc.);
a selenazole nucleus (e.g., 4-methylselenazole nucleus, 4-nitroselenazole nucleus, 4-phenylselenazole nucleus, etc.,);
a benzoselenazole nucleus (e.g., benzoselenazole nucleus, 5-chlorobenzoselenazole nucleus, 5-nitrobenzoselenazole nucleus, 5-methoxybenzoselenazole nucleus, 5-hydroxybenzoselenazole nucleus, 6-nitrobenzoselenazole nucleus, 5-chloro-6-nitrobenzoselenazole nucleus, etc.);
a napthoselenazole nucleus (e.g., onaphtho[2,1-d]selenazole nucleus, naphtho[1,2-d]selenazole nucleus, etc.);
a 3,3-dialkylindolenine nucleus (e.g., 3,3-dimethylindolenine nucleus, 3,3-diethylindolenine nucleus, 3,3-dimethyl-5-cyanoindolenine nucleus, 3,3-dimethyl-6-nitroindolenine nucleus, 3,3-dimethyl-5-nitroindolenine nucleus, 3,3-dimethyl-5-methoxyindolenine, 3,3'-dimethyl-5-methylindolenine, 3,3-dimethyl-5-chloroindolenine, etc.);
an imidazole nucleus (same as the imidazole nuclei illustrated relative to formula I);
a pyridine nucleus (e.g., 2-pyridine nucleus, 4-pyridine nucleus, 5-methyl-2-pyridine nucleus, 3-methyl-4-pyridine nucleus, etc.);
a quinoline nucleus (e.g., 2-quinoline nucleus, 3-methyl-2-quinoline nucleus, 5-ethyl-2-quinoline nucleus, 6-methyl-2-quinoline nucleus, 6-nitro-2-quinoline nucleus, 8-fluoro-2-quinoline nucleus, 6-methoxy-2-quinoline nucleus, 6-hydroxy-2-quinoline nucleus, 8-chloro-2-quinoline nucleus, 4-quinoline nucleus, 6-ethoxy-4-quinoline nucleus, 6-nitro-4-quinoline nucleus, 8-chloro-4-quinoline nucleus, 8-fluoro-4-quinoline nucleus, isoquinoline nucleus, 6-nitro-1-isoquinoline nucleus, 3,4-dihydro-1-isoquinoline nucleus, 6-nitro-3-isoquinoline nucleus, etc.);
an imidazo [4,5-b]quinoxaline nucleus (same as the imidazo[4,5-b]quinoxaline nuclei illustrated relative to formula I);
an oxadizaole nucleus, a thiadiazole nucleus, a tetrazole nucleus, a pyrimidine nucleus, etc.

$R_6$ has the same meaning as R or $R_1$ defined in formula I.

$Q_4$ represents a non-metallic atomic group necessary for completing a 5-membered or 6-membered nitrogen-containing heterocyclic nucleus, the hetero atoms being selected from nitrogen, selenium, sulfur and oxygen. Examples of the heterocyclic nucleus are:

- a 2-pyrazolin-5-one nucleus (e.g., 3-methyl-1-(4-carboxyphenyl-2-pyrazolin-5-one nucleus, 1-(4-carboxyphenyl)-2-pyrazolin-5-one nucleus, 1-(5-carboxybenzothiazol-2-yl)-3-methyl-2-pyrazolin-5-one nucleus, etc.);
- a barbituric acid nucleus or 2-thiobarbituric acid nucleus (e.g., a barbituric acid nucleus or 2-thiobarbituric acid nucleus containing 1-(4-carboxyphenyl) group, 1-carboxymethyl group, etc.);
- a rhodanine nucleus (e.g., 3-carboxymethylrhodanine nucleus, 3-(2-carboxyethyl)rhodanine nucleus, 3-(4-carboxybutyl) rhodanine nucleus, 3-(4-carboxyphenyl)rhodanine nucleus, etc.,);
- a 2-thio-2,4-oxazolidinedione nucleus (e.g., 3-(3-carboxypropyl)-2-thio-2,4-oxazolidinedione nucleus, etc.);
- a 2,4-thiazolidinedione nucleus (e.g., 3-(4-carboxyphenyl)-2,4-thiazolidinedione nucleus, etc.);
- a thiazolidinone nucleus (e.g., 3-(4-carboxyphenyl)-4-thiazolidinone nucleus, etc.);
- an isooxazolone nucleus (e.g., 3-(4-carboxyphenyl)-5-(4H)-isooxazolone nucleus, 3-(2-carboxyethyl)-5-(4H)-isooxazolone nucleus, etc.);
- a 2,4-imidazolidinedione nucleus (hydantoin nucleus) (e.g., 3-carboxymethyl-2,4-imidazolidinedione nucleus, 3-(2-carboxyethyl)-2,4-imidazolidinedione nucleus, 3-(4-carboxyphenyl)-2,4-imidazolidinedione nucleus, etc.);
- a 2-thio-2,4-imidazolidinedione nucleus (e.g., 3-carboxymethyl-2-thio-2,4-imidazolidinedione nucleus, 3-(2-carboxyethyl)-2-thio-2,4-imidazolidinedione nucleus, 3-(4-carboxyphenyl)-2-thio-2,4-imidazolidinedione nucleus, 3-(4-carboxyphenyl)-1-ethyl-2-thio-2,4-imidazolidinedione nucleus, etc.,);
- a 2-imidazolin-5-one nucleus (e.g., 2-carboxymethyl-2-imidazolin-5-one nucleus, etc.), etc.

$R_5$ is a substituent on $Z_3$ and represents $-P_i-Q_j-COOH$ (wherein, P and Q have the same meaning as P and Q defined relative to formula (I) and i and j, which may be the same or different, each represents 0 or 1.

In the formulae above, unless otherwise indicated, a group of alkyl or aliphatic nature (including a substituent, if any, and also including the alkyl moiety present in an alkoxy group, a dialkylamino group, etc.) generally has 1 to 12 carbon atoms, preferably 1 to 5 carbon atoms in total, and a group of aryl or aromatic nature (including a substituent, if any, and also including the aryl moiety present in an aryloxy group, a diarylamino group, etc.) generally has 6 to 18 carbon atoms, preferably 6 to 11 carbon atoms.

In the merocyanine dyes shown by above described formula II—II having a carboxy group and the cyanine dyes shown by formula I, the cyanine dyes each having a carboxy group at any position on the cyanine chromophore nuclei except on N therein are excellent as the dyes for producing the enzyme activity measuring synthetic substrate used in this invention from the points of reaction efficiency and solubility.

Preferred specific examples of spectrally sensitizing dyes used in this invention are given below:

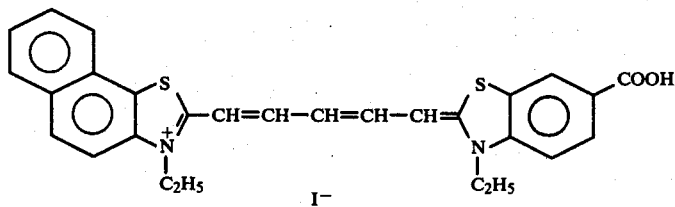

(I-1)

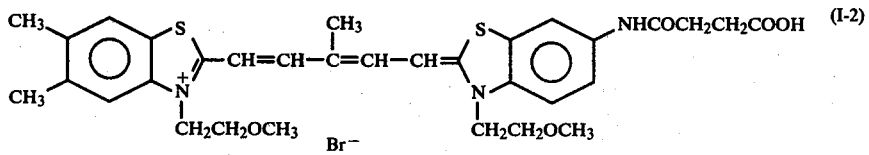

(I-2)

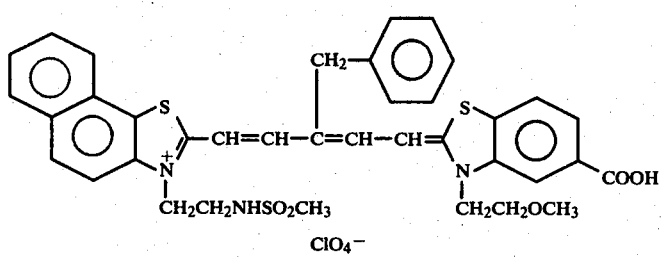

(I-3)

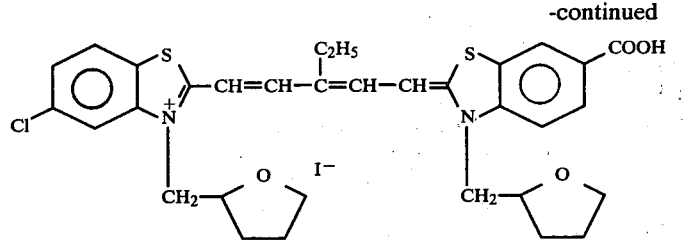
(I-4)
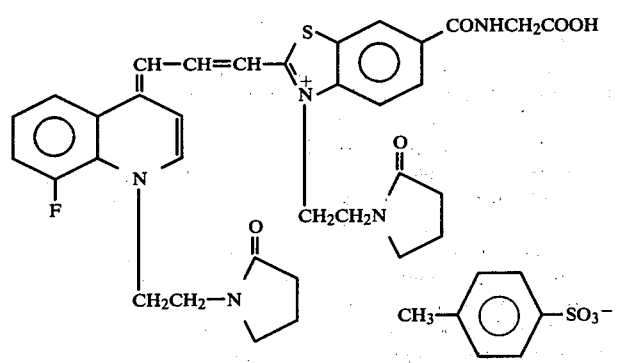
(I-5)
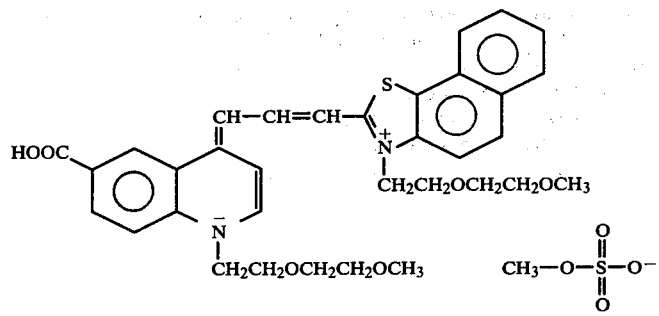
(I-6)
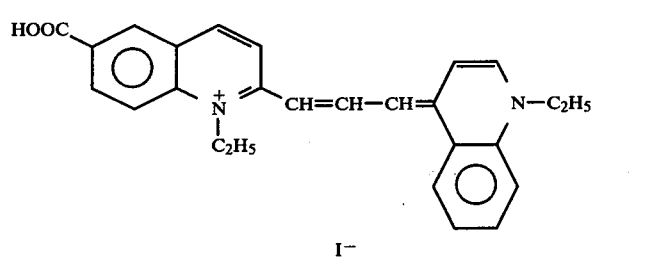
(I-7)
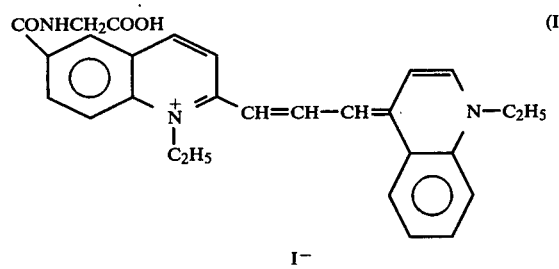
(I-8)
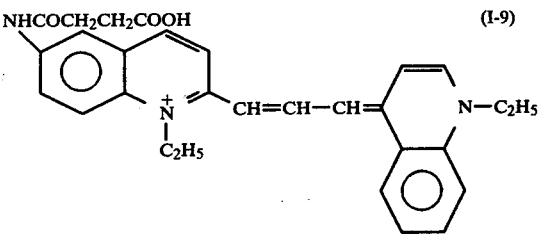
(I-9)
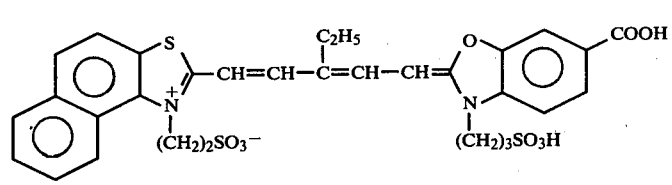
(I-13)

-continued
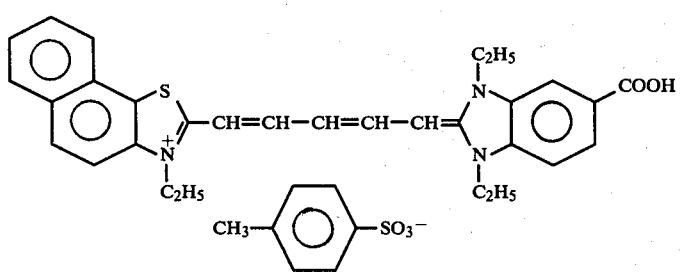
(I-14)
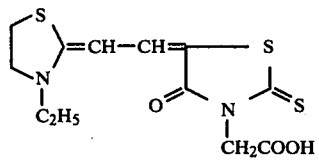
(II-1)
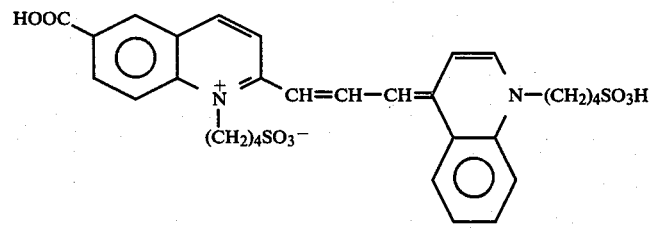
(I-10)
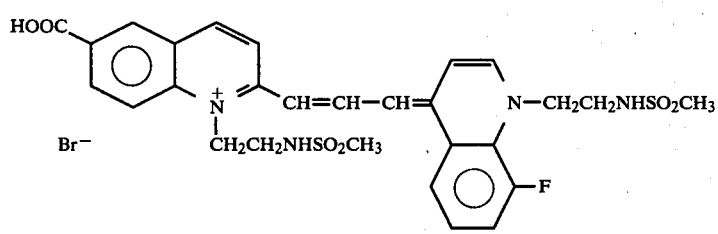
(I-11)
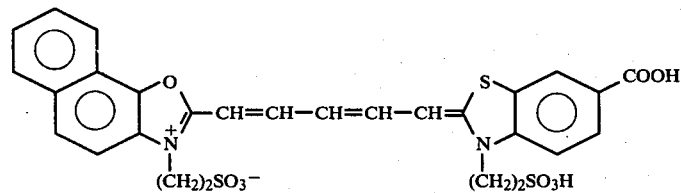
(I-12)
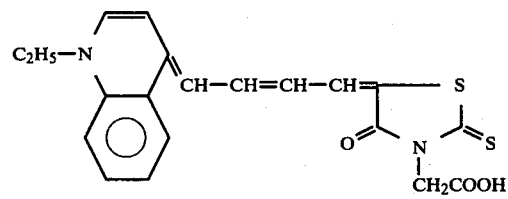
(II-2)
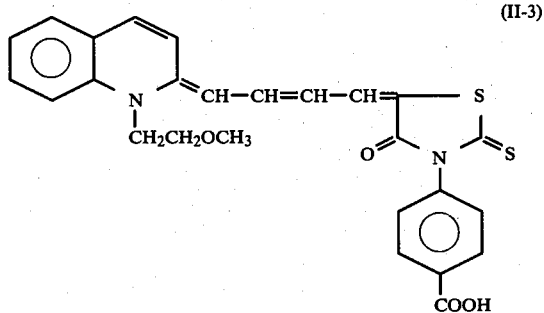
(II-3)
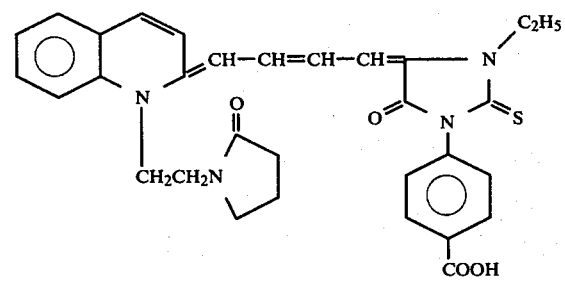
(II-4)
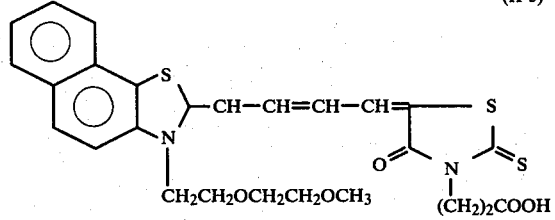
(II-5)

-continued
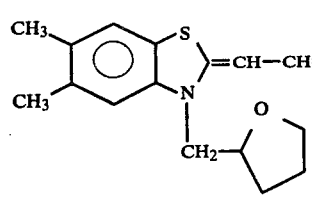 (II-6)
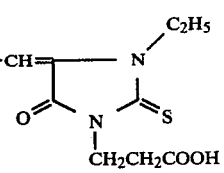
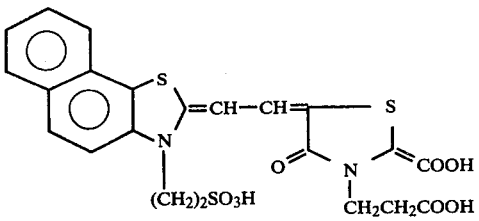 (II-7)
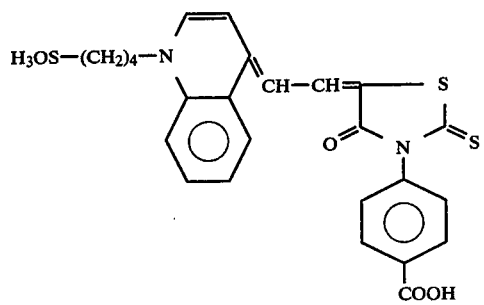 (II-8)
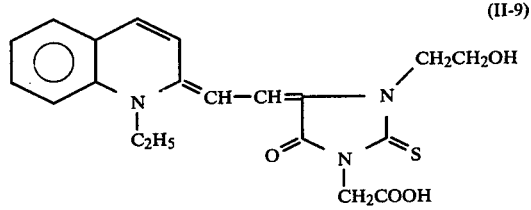 (II-9)
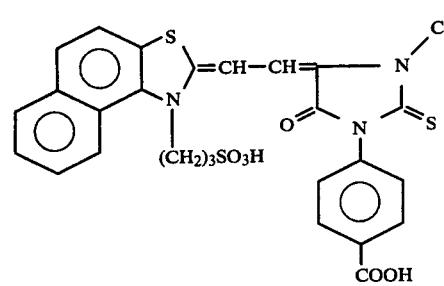 (II-10)
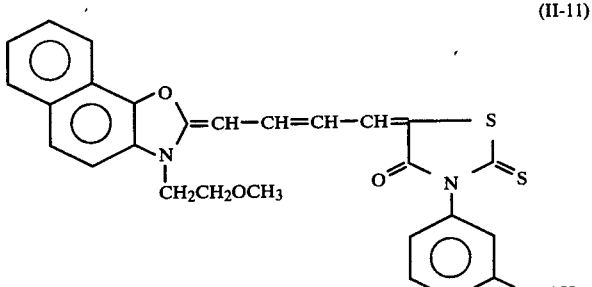 (II-11)
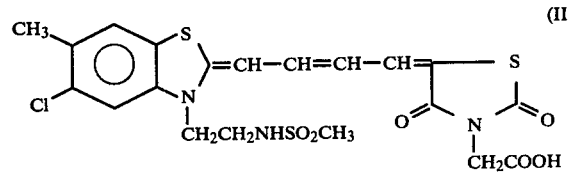 (II-12)
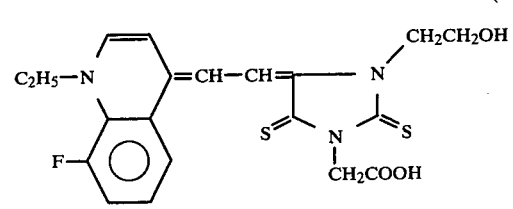 (II-13)
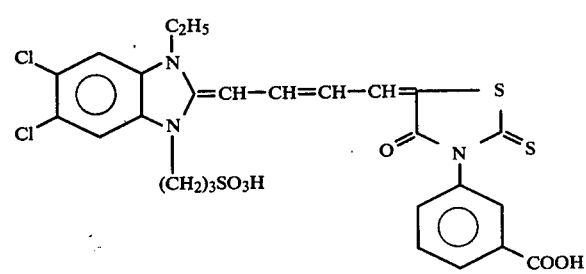 (II-14)
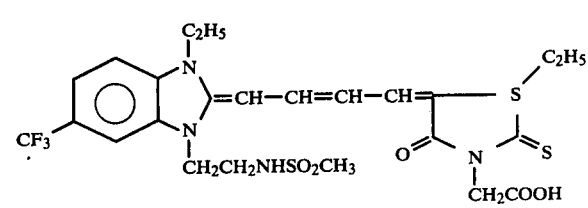 (II-15)

-continued

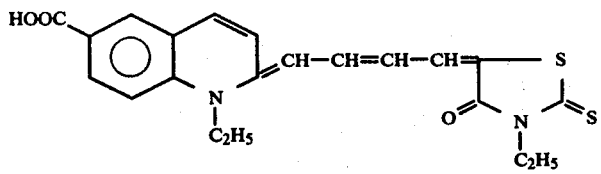

(II-16)

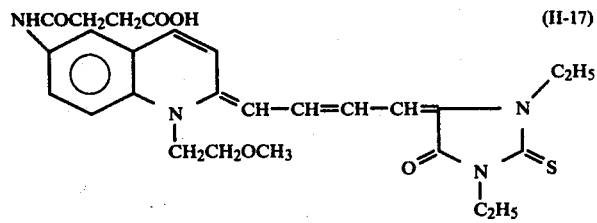

(II-17)

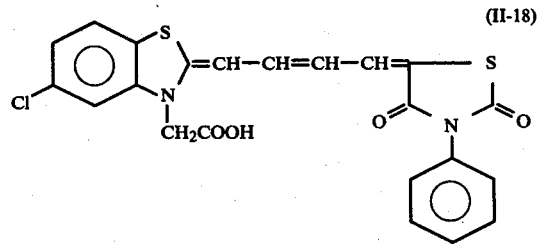

(II-18)

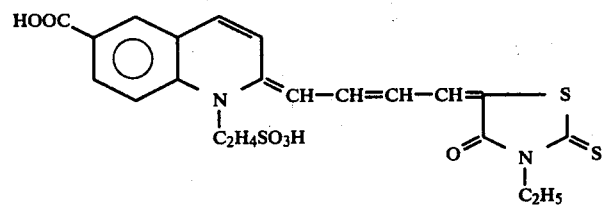

(II-19)

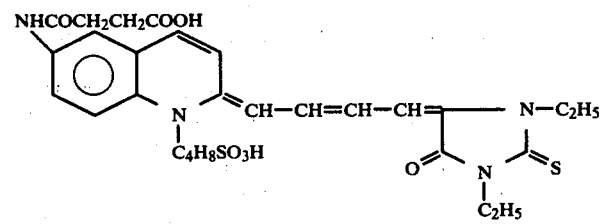

(II-20)

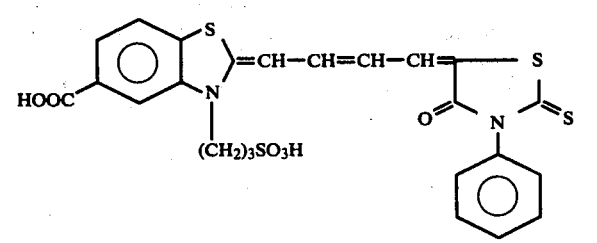

(II-21)

These compounds, including syntheses thereof, are described in F. M. Hamer, CYANINE DYES AND RELATED COMPOUNDS, published by Interscience Publishers (1964).

The amount of spectral sensitizer used for labelling varies depending upon the kind of the aforesaid substances to be labelled, but is generally in a molar ratio of 1/100 to 100 moles per 1 mole of the antigen or antibody, preferably 1/20 to 20 times, more preferably ½ to 2 times, some basis.

As methods for confirming completion of labelling, methods for measuring spectra such as UV, visible rays, IR, mass and NMR spectra, etc., and a method confirming labelling via disappearance of the terminal group at which the labelling substance is to be introduced, are representative. Simple tests will be enough to confirm completion of labelling. Where it is confirmed utilizing absorption spectrum, following completion of the labelling reaction, an absorption spectrum of a separated and purified product is measured; if the resulting absorption spectrum is consistent with the intrinsic absorption spectrum which a spectral sensitizer possesses, it is confirmed that the labelling reaction be effected. A further method for confirming the labelling being effected is to analyze for the presence or absence of the specific terminal grups, e.g., an amino or carboxy group(s). In case that the spectral sensitizer is introduced at the terminal amino group(s) of the spectral sensitizer, it is confirmed by the analysis of the N-terminal that completion of the labelling reaction has been effected if the corresponding amino acid(s) to an amino group(s) on which labelling is to occur are not detectable. Detailed disclosure on such N terminal analysis is described in, e.g., B. S. Hartley and V. Massey, Biochim. Biophys. Acta, 21, 58 (1956) (generally referred to as a Dansyl method in the art), Archn. Biochem. Biophys., 22, 475 (1949) (a PTC (phenol isocyanate) method), F. Sanger, Biochem. J., 39, 507 (1945) (a dinitrofluorobenzene method), etc. In a similar manner, the terminal carboxy group(s) are analyzed to check completion of the labelling reaction, details of which are given in, e.g., S. Akabori, K. Ohno and K. Narita, Bull. Chem. Soc. Japan, 25, 214 (1952) (generally referred to as a hydrazine decomposition method in the art), H. Matuo, U. Fujimoto and T. Tatuno, *Biochem. Biophys. Res. Communication*, 22, 69 (1966) (a tritium marking method), etc. Further, details of these terminal determination methods are also given as a review in S. B. Needleman, *PROTEIN SEQUENCE DETERMINATION*, published by Springer Verlag (Berlin), 1975.

In the case of detecting, in particular, a hydrolase type enzyme in the method of this invention, there can be used immobilized substrate prepared by binding the aforesaid synthetic substrate to a chromatographic carrier, e.g., a latex, polymer beads, plastic chips, glass beads, dextran gel, starch gel, microcapsules, chromatographic carriers such as ion exchange resins, etc., filter paper or the like.

The hydrolase type enzyme used herein includes, e.g., protease, nuclease, glycogenase, lipase, esterase, etc. and is classified into a so-called endo type wherein the substrate specificity is present at the center of the substrate molecule, and a so-called exo type wherein the substrate specificity is present at the terminal of the substrate molecule, respectively. Contact sites of respective enzymes are described in detail in *DATABOOK OF BIOCHEMISTRY*, first & second volumes, edited by the Biochemical Association, Japan, published by Tokyo Kagaku Dojin, 1979 and 1980, P. D. Boyer, *The Enzyme*, vols. 3, 4 & 5 (1971) Academic Press.

In the method of this invention, an immobilized substrate described above and a high molecular substrate as will be later described are not very effective for exo-type enzymes as to the contact mode. Further, the immobilized substrate used in this invention must meet the requirement that the bond to be specifically decomposed or cleaved by the enzyme to be measured is disposed or inserted between the carrier used for immobilization and spectral sensitizer structure (B). Further, in the case of immobilizing the synthetic substrate it is necessary to take care not to inhibit the action of the enzyme by steric hindrance and, in many cases, it is desirable to insert a spacer (e.g., linking group (C) as used for producing the synthetic substrate) between the functional group or the carrier and the immobilized substrate. The carrier may be in the form of, for example, a plate, a rod, a granule, a fiber or coating.

By the use of such an immobilized substrate, a low molecular weight substance containing spectral sensitizer structure (B) is released in the reaction solution by the enzymatic reaction (hydrolysis), whereby the separation of the spectral sensitizer structure from the unreacted synthetic substrate on the carrier becomes unnecessary or extremely easy.

Further, for the reasons as described above, in the method of this invention, a high molecular weight synthetic substrate to which a number of mols of a spectral sensitizer structure are linked per 1 mol of the high molecular synthetic substrate via structure (A) specifically cleaved or decomposed with an enzyme to be measured can be employed for assaying hydrolase enzymes other than exo-type hydrolases. As the fundamental structure of such a high molecular substrate, there are generally structures where the main chain per se of a polymer consists of a repeat of structure (A) (e.g., as in a natural high molecular substrate such as cellulose for cellulase, soluble starch for amylase, protein for protease, nucleic acid for nuclease, etc.) and spectral sensitizer structure (B) forms a side chain(s) thereof from the main chain of the polymer directly or via linking group (C) and a structure where the main chain of the polymer does not possess structure (A) but spectral sensitizer structure(s) (B) forms side chains from the main chain of the polymer via structure (A) to be cleaved. In any case, the enzyme reaction product containing spectral sensitizer structure (B) having a reduced molecular weight is formed as a result of the enzymatic reaction, which can easily be separated from the unreacted synthetic substrate.

In both the case of using the immobilized synthetic substrate and the case of using the high molecular synthetic substrate, it is preferred in this invention to use as the spectral sensitizer structure to be assayed by bringing the same into contact with silver halide, the reaction product of which is released or changed to a lower molecular weight, as a result of the enzymatic reaction.

According to the method of this invention, a plurality of enzymes contained in a test sample can be discriminatively and/or simultaneously detected. That is, as a specific method for discriminatively assaying tow or more enzymes, there is a method wherein a substrate fitting only one kind of enzyme among a plurality of enzymes is used utilizing the specificity of the enzyme, a method wherein a substrate is endowed with the specificity to an enzyme by controlling the reaction conditions (e.g., reaction pH, reaction temperature, ionic strength, etc.), a method wherein the measurement of an enzyme is performed in the presence of inhibitors or inactivators specific to enzymes other than the enzyme to be measured, and a method comprising a combination of these methods.

The term "inhibitor" used herein refers to a material which inhibits the function of the enzyme by a reversible change while the term "inactivator" refers to a material which inhibits and inactivates the function of the enzyme by an irreversible change. The inhibitor and the inactivator to each enzyme are described along with the specificity in *DATABOOK OF BIOCHEMISTRY*, first and second separate volumes, edited by the Biochemical Association, Japan, published by Tokyo Kagaku Dojin, 197- and 1980, *The Enzyme*, P. D. Boyer, vols. 3, 4 and 5 (1971), Academic Press, New York, etc.

Further, as practical methods for simultaneously measuring two or more enzymes discriminatively, there are, for example, the methods described below:

(1) A method wherein, after performing enzyme reactions using substrates each composed of a spectrally sensitizing dye structure (B) having a distinguishable spectrally sensitizing wavelength from those of any other spectrally sensitizing dye structure or structures linked to each structure (A), which is specifically contacted with an enzyme in two or more enzymes to be measured in unitary correspondence, the spectrally sensitizing dye-containing materials containing either the reaction product(s) containing the spectrally sensitizing dye structure(s) and the unreacted synthetic substrate(s) with the enzyme to be measured is contacted with a silver halide, they are separately each exposed to light having a sensitizing wavelength region corresponding to each spectrally sensitizing dye structure contained in the reaction product or the substrate corresponding to each enzyme followed by development, the density of the developed silver and/or colored dye is measured, and the activity of each component enzyme is determined from the measured value by calculation.

(2) A method where enzyme reactions are performed using a synthetic substrate having common specificities to two or more enzymes with the progress of the reaction, the total activities of the whole component enzymes are measured after a certain period of time since the initiation of the reaction and, at the same time, an inhibitor or inactivator acting specifically to only one component enzyme of the plural component enzymes is added followed by measuring the total activities, the above procedure is repeated in accordance with the number of enzymes, and the activity of each component enzyme is determined from the difference between the total activities before the addition of the inhibitor or inactivator and the activities after the addition thereof at each measured time.

(3) A method where enzyme reactions are performed using plural synthetic substrates different from each other, each of which corresponds unitarily to each enzyme in the plural enzymes to be measured and each of which forms a spectrally sensitizing dye structure (B)-containing product having a different structure from any other product by an enzyme reaction, either each sensitizing dye structure (B)-containing product or unreacted synthetic substrate corresponding to each enzyme being separated by an appropriate separation method (e.g., liquid chromatography, etc.) utilizing the difference in physicochemical properties between the plural sensitizing dye structure (B)-containing reaction products and/or plural unreacted synthetic substrates and then being brought into contact with silver halide, whereafter they are exposed to light of each spectrally sensitizing wavelength region followed by development and the density of developed silver and/or colored dye is measured, whereby the activity of each enzyme is determined. The above procedure is repeated by the number of the enzymes to be measured.

(4) A method composed of a combination of the above described methods.

In the first method among the above described methods of simultaneously discriminating and determining two or more enzymes, it is preferred, to minimize errors, to use a combination of two or more spectrally sensitizing dyes having different spectrally sensitizing wavelength regions or at least having low overlap between their spectrally sensitizing wave length region.

For example, in the case of using two sensitizing dyes, it is preferred to select a combination of dyes one of which has a sensitization maximum at a wavelength longer than 630 nm and the other of which has a sensitization maximum at a wavelength shorter than 630 nm, said two sensitization maximums being spaced apart from each other by more than 50 nm.

Also, in the case of using three kinds of sensitizing dyes, it is preferred to select a combination of, for example, the above described two sensitizing dyes and a third sensitizing dye having its sensitization maximum at a wavelength longer than 750 nm.

In any mode of the method of this invention described above, it is convenient to employ, if desired or necessary, such a method that after stopping the enzyme reaction using appropriate conditions to stop the enzyme reaction (e.g., by increasing or decreasing the reaction pH, or by elevating or lowering the reaction temperature, etc.), or, using an enzyme inhibitor or inactivator or a modifier (e.g., urea, guanidine hydrochloride, or a surface active agent having a modifying action such as SDS, etc.) which is also an inactivator in a broad sense, either the reaction product containing spectral sensitizer structure (B) or the unreacted synthetic substrate is brought into contact with silver halide.

In this invention, the activity of an enzyme is measured by bringing either the spectrally sensitizing dye structure (B)-containing reaction product formed by the enzyme reaction or the unreacted synthetic substrate into contact with a silver halide, and for practicing the above described procedure, there are two basic procedures:

(1) A liquid containing the above described component is dropped into a silver halide photographic emulsion containing unexposed silver halide grains and adsorbed on the grains. The mixture is placed in a transparent cell, exposed to light of spectrally sensitizing wavelength, a photographic developer is added to the mixture to blacken the exposed silver halide grains, and then optical density is measured.

(2) At least one silver halide emulsion layer containing unexposed silver halide grains is coated on a support and a liquid containing the above described component is dropped onto the emulsion layer, whereby the liquid permeates into the emulsion layer and is adsorbed on the silver halide grains in the emulsion layer. Then, the emulsion layer is exposed to light of sensitizing wavelengths from the emulsion layer side or the support side if the support is transparent immersed in a photographic developer to blacken the exposed silver halide grains, and then optical density is measured.

Among the above described methods, method (2) is particularly preferred and is convenient for determining plural enzymes. That is, plural reaction products containing the spectral sensitizing dye strucutres (B) or plural unreacted synthetic substrates are separated from each other, spotted or dropped on the emulsion layer in at least the number of the enzymes to be determined, each spot is exposed to light of each spectrally sensitizing wavelength, the emulsion layer is then immersed in a developer to blacken the spot or drop portions, and the optical density or degree of blackening is measured.

When color development is performed in the above described methods, the optical density of the colored dye is measured and when a filter is used in this case, the extent of blackening and the optical density of the colored dye are measured.

In method (2), it is preferred to use a transparent film such as a cellulose acetate film or a polyester film as the support for the silver halide emulsion layer and expose the silver halide emulsion layer from the support side. In this case it is convenient to form a light absorbing layer which transmits light of the spectrally sensitizing wave length but absorbs light of other wave lengths, in particular light of the intrinsic sensitivity region of the silver halide emulsion between the silver halide emulsion layer and the light source as an inner filter. The light absorbing layer may be formed between the silver halide emulsion layer and the support, may be a dyed support itself, or may be formed on the opposite surface of the support to the silver halide emulsion layer.

The silver halide emulsions used in this invention may be prepared by the methods described in, for example, Trivelli & Smith, *The Photographic Journal*, Vol. 79, 330-338(1939); C. E. K. Mees, *The Theory of the Photographic Process* published by Macmillan; and Glafkides, *Photographic Chemistry*, Vol. 1, pages 327-336 (Fountain Press).

As a more preferred embodiment of measuring the enzyme activity in both the above described cases (1) and (2) of the method of this invention, there is a method of adsorbing either the enzyme reaction product containing the spectrally sensitizing dye structure (B) or the unreacted synthetic substrate on silver halide in the presence of a hydrazine compound shown by following formula (H) and exposing to light of the necessary spectrally sensitizing wavelength followed by development. The hydrazine compound may be in a testing sample or spotted or dropped liquid, or may be previously added to the silver halide emulsion light sensitive element, or be present in a developer. Also, antifoggant may be used in each step.

By employing the aforesaid preferred method, the density of developed silver or colored dye in the spot portion as compared to the density in blank areas greatly increases as compared with the case of not using the hydrazine compound at the same spectrally sensitizing dye concentration, same exposure amount and same development conditions, whereby detection sensitivity increases and enzyme activity can be measured at a higher sensitivity.

The hydrazine compound which is employed in accordance with the method of this invention is represented by formula (H):

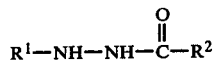
(H)

$R^1$: an aryl group which may be substituted
$R^2$: a hydrogen atom, an alkyl group which may be substituted or an aryl group which may be substituted.

Further detailed description will be given with respect to the compound represented by formula (H), wherein an alkyl or aliphatic group (including a substituent if any and also including the alkyl moiety present in an alkoxy group, a dialkylamino group, etc.) generally has 1 to 12 carbon atoms in total, preferably 1 to 5 carbon atoms, and an aryl or aromatic group (including a substituent if any and also including the aryl moiety present in an aryloxy group, an aryloxycarbonyl group, etc.) generally has 6 to 18 carbon atoms in total, preferably 6 to 11 carbon atoms, unless otherwise indicated.

The aryl group represented by $R^1$, which may be substituted, is a monocyclic or bicyclic aryl group. Examples are a benzene ring and a naphthalene ring. Particularly preferred ones are those containing a benzene ring.

The aryl group may be substituted. Preferred examples of such substituents are shown below:

(1) Straight, branched and cyclic alkyl groups, preferably containing 1 to 20 carbon atoms, such as a methyl group, an ethyl group, an isopropyl group, an n-dodecyl group, and a cyclohexyl group;

(2) Aralkyl groups, preferably monocyclic and bicyclic aralkyl groups having an alkyl moiety containing 1 to 3 carbon atoms, such as a benzyl group;

(3) Alkoxy groups, preferably containing 1 to 20 carbon atoms, such as a methoxy group and an ethoxy group;

(4) Amino groups, preferably an —NH$_2$ group and those amino groups mono- or di-substituted by an alkyl group containing 1 to 20 carbon atoms, such as a dimethylamino group and a diethylamino group;

(5) Aryloxy groups, preferably a phenoxy group;
(6) Groups represented by A—X—(Y)$_n$—
(7) Groups represented by

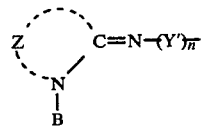

(8) Groups represented by $R^3$ CONHNH—Ar—Y″—.

In the formula: A—X—(Y)$_n$— as illustrated above, Group (6):

(a) X is a divalent linking group selected from the following $x_1$ to $x_{11}$: $x_1$=—CSNH—, $x_2$=—S—CSNH—,

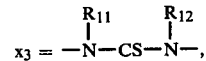

$x_4$=—CONH—, $x_5$=—O—E—CONH—,

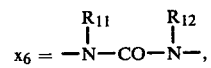

$x_7$=—NHCO—, $x_8$=—O—, $x_9$=—SO$_2$NH—, $x_{10}$=—E—NH—, and $x_{11}$=—E=N—;

(b) Y is a divalent linking group selected from the following $y_1$ to $y_{11}$: $y_1$=—CONH—, $y_2$=—E—CONH—, $y_3$=—E—, $y_4$=—E—O—E′—, $y_5$=—E—S—E′—, $y_6$=—SO$_2$NH—, $y_7$=—E—SO$_2$NH—, $y_8$=—NHCONH—, $y_9$=—E—NHCONH—, $y_{10}$=—E—O—E′—CONH—, and $y_{11}$=—E—E′—, wherein $R_{11}$ is a hydrogen atom, an aliphatic group (preferably, an alkyl group containing 1 to 20 carbon atoms, a cycloalkyl group containing 3 to 12 carbon atoms, or an alkenyl group containing 2 to 20 carbon atoms), or an aromatic group (preferably, a phenyl group and a naphthyl group), $R_{12}$ is a hydrogen atom or an aliphatic group represented by $R_{11}$, $R_{11}$ and $R_{12}$ may combine with each other to form a ring, with preferred examples of such ring being

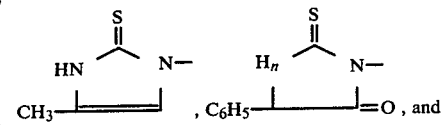

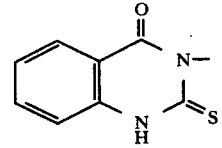

(in this case, A represents hydrogen),
when $R_{11}$ and $R_{12}$ do not form a ring, any one of $R_{11}$ and $R_{12}$ is a hydrogen atom, and
E and E′ each represents a saturated or unsaturated divalent aliphatic group (e.g., an alkylene group, such as an ethylene group and a 1-methylpropylene group, and an alkenylene group, such as a propenylene group and a butenylene group), a divalent aromatic group (e.g., a phenylene group, a naphthylene group and a 5-amino-1,2-phenylene group), with the exception that in $y_{11}$=—E—E′—, E and E' are divalent groups different from each other and in $x_{11}$=—E=N—, E is —(CH$_2$)$_m$—CH= (wherein m is an integer of 0 to 2);

(c) n is an integer of 0 or 1, and when n is 1, particularly preferred combinations of X and Y are $x_3$-$y_2$, $x_7$-$y_2$, $x_8$-$y_2$, $x_{12}$-$y_3$, $x_3$-$y_7$, $x_5$-$y_9$, $x_9$-$y_9$, and $x_3$-$y_{10}$; and (d) A represents a straight, branched or cyclic alkyl group (preferably containing 1 to 20 carbon atoms, such as a methyl group, a propyl group, and an n-hexyl group), a monocyclic or bicyclic aryl group (e.g., a phenyl group), a monocyclic or bicyclic aralkyl group (preferably containing 7 to 26 carbon atoms, such as a benzyl group), and a heterocyclic radical.

The heterocyclic radical represented by A is a 5- or 6-membered ring containing therein at least one hetero atom and may be condensed with an aromatic ring, particularly a benzene ring. Particularly, a heterocyclic radical containing at least one nitrogen atom is preferred. Examples are a thiazolyl group, a benzthiazolyl group, an imidazolyl group, a thiazolinyl group, a pyridinyl group, a tetrazolyl group, a benztriazolyl group, an indazolyl group, a benzimidazolyl group, a hydroxytetrazainden-2 or 3-yl group; mercapto group-containing heterocyclic groups, such as 2-mercaptobenzthiazolyl group and a 2-mercaptobenzoxazolyl group; and quaternary nitrogen atom-containing heterocyclic radicals, such as 2-methylbenzthiazolinium-3-yl, 2-(N-sulfoethylbenzthiazolinio), and N,N-dimethylbenzimidazolinium-2-yl.

The foregoing groups represented by A may be substituted. Examples of such substituents include:
an alkoxy group (preferably containing 1 to 18 carbon atoms, such as a methoxy group),
an alkoxycarbonyl group (preferably containing 2 to 19 carbon atoms, such as an ethoxycarbonyl group),
a monocyclic or bicyclic aryl group (e.g., a phenyl group),
an alkyl group (preferably containing 1 to 20 carbon atoms, such as a methyl group and a tert-amyl group),
a dialkylamino group (preferably containing 1 to 20 carbon atoms, such as a dimethylamino group),
an alkylthio group (preferably containing 1 to 20 carbon atoms, such as a methylthio group),
a mercapto group, a hydroxy group, a halogen atom, a carboxy group, a nitro group, a cyano group,
a sulfonyl group (preferably containing 1 to 20 carbon atoms, such as a methylsulfonyl group), and
a carbamoyl group (preferably containing 1 to 20 carbon atoms, such as a carbamoyl group and a dimethylcarbamoyl group).

In the foregoing group represented by Group (7)

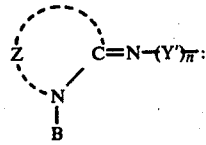

(a) Z is a group of non-metallic atoms and combines with

to form a 5- or 6-membered heterocyclic ring, with suitable examples of such 5- or 6-membered heterocyclic rings being a thiazoline ring, a benzthiazoline ring, a naphthothiazoline ring, a thiazolidine ring, an oxazoline ring, a benzoxazoline ring, an oxazolidine ring, a selenazoline ring, a benzselenazoline ring, an imidazoline ring, a benzimidazoline ring, a tetrazoline ring, a triazoline ring, a thiadiazoline ring, a 1,2-dihydropyridine ring, a 1,2-dihydroquinone ring, a 1,2,3,4-tetrahydroquinoline ring, a perhydro-1,3-oxazine ring, a 2,4-benz[d]oxazine ring, a perhydro-1,3-thiazine ring, a 2,4-benz[d]thiazine ring and a uracyl ring;

(b) B is a hydrogen atom or a saturated or unsaturated aliphatic group [such as an alkyl group (preferably containing 1 to 20 carbon atoms, e.g., a methyl group and an ethyl group), an alkenyl group (preferably containing 2 to 22 carbon atoms, e.g., an allyl group), and an alkynyl group (preferably containing 2 to 20 carbon atoms, e.g., a butynyl group)], which may be substituted by an alkoxy group, an alkylthio group, an acylamino group, an acyloxy group, a mercapto group, a sulfo group, a carboxy group, a hydroxy group, a halogen atom, an amino group, or the like;

(c) Y' has the same meanings as described for Y in Group (6); and (d) n is 0 or 1.

In the group represented by the formula: R$^3$CONHNH—Ar—Y"—, Group (8):

(a) R$^3$ is the same as R$^2$ as described hereinafter;

(b) —Ar— represents a divalent aryl group, preferably a phenylene group, which may be substituted; and (c) Y" is the same as Y described in Group (6), with divalent linking groups represented by y$_3$ to y$_5$ being particularly preferred.

In formula (H), R$^2$ is a hydrogen atom, an alkyl group which may be substituted, or an aryl group which may be substituted. Substituents which can be used include a halogen atom, a cyano group, a carboxy group, and a sulfo group. Examples of such alkyl and aryl groups are a methyl group, an ethyl group, an n-propyl group, an isopropyl group, a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group, and a 2,5-dichlorophenyl group.

Of the substituents represented by R$^2$, a hydrogen atom, a methyl group and a phenyl group (including a substituted phenyl group) are preferred, and a hydrogen atom is particularly preferred.

Preferred examples of the compounds represented by formula (H) are described in U.S. Pat. Nos. 4,168,977 and 4,224,401 and British Pat. No. 1,558,946, Japanese Patent Application (OPI) Nos. 52050/80 and 90940/80, *Research Disclosure*, No. 17626 (Vol. 176, 1978), etc. Of these compounds, those described in U.S. Pat. Nos. 4,168,977 and 4,224,401 are particularly preferred.

Specific examples of compounds represented by formula (H) are shown below, but this invention is not limited only thereto.

Compound H-1

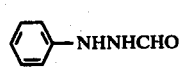

Compound H-2

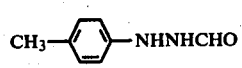

-continued
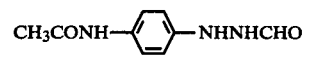
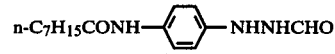
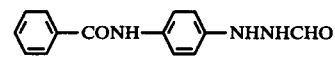
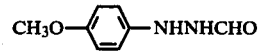
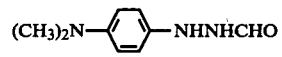
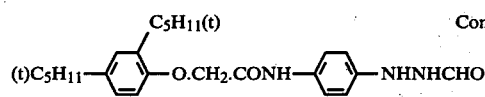
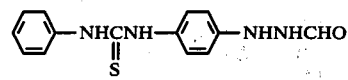
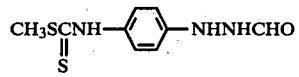
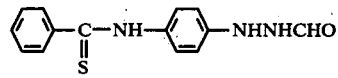
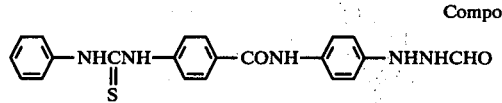
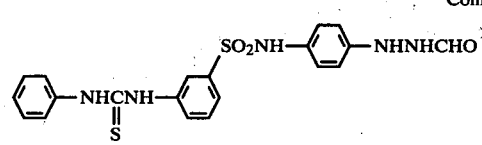
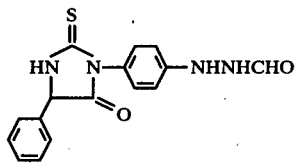
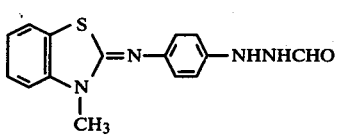
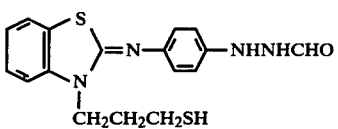
-continued
Compound H-3
Compound H-4
Compound H-5
Compound H-6
Compound H-7
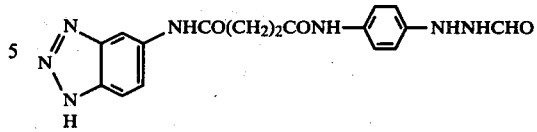
Compound H-8
Compound H-9
Compound H-10
Compound H-11
Compound H-12
Compound H-13
Compound H-14
Compound H-15
Compound H-16
Compound H-17
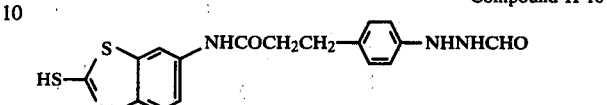
Compound H-18
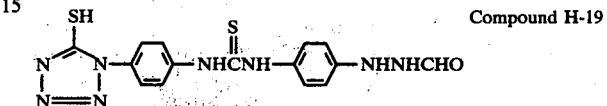
Compound H-19
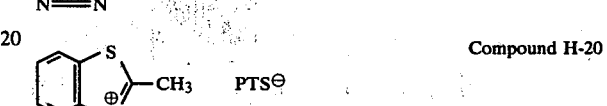
Compound H-20
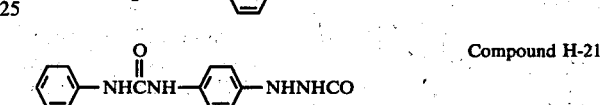
Compound H-21
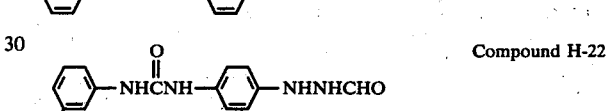
Compound H-22
Compound H-23
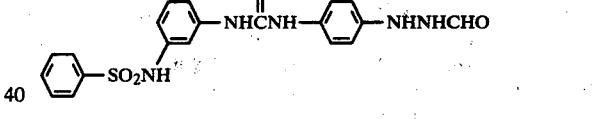
Compound H-24
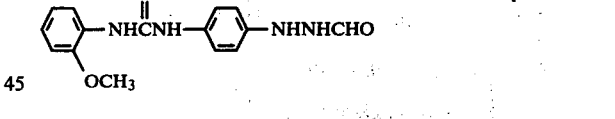
Compound H-25
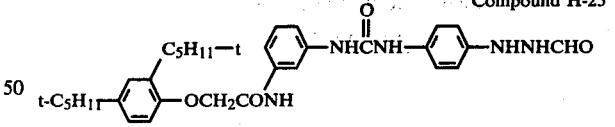
Compound H-26
Compound H-27
Compound H-28
Compound H-29
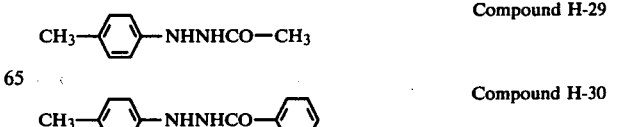
Compound H-30

-continued

Compound H-31

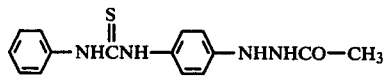

Compound H-32

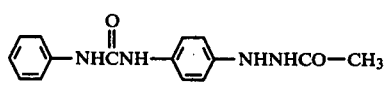

These compounds can be synthesized by methods as described in U.S. Pat. Nos. 4,168,977 and 4,224,401, and British Pat. No. 1,558,946, Japanese Patent Application OPI Nos. 20921/78, 20922/78, 66732/78 and 20318/78, all of which are incorporated herein by reference. Particularly preferred compounds are those described in Japanese Patent Application OPI Nos. 20921/78, 20922/78 and 66732/78.

In the case of incorporating the compound shown by formula (H) in a silver halide light sensitive element, the amount thereof if $10^{-8}$ to $10^{-1}$ mole per mole of silver, preferably $10^{-6}$ to $5 \times 10^{-2}$ mole per mole of silver. In the case of incorporating the compound in a photographic pre-bath, a developer or a buffer solution used for the enzyme reaction, the amount of 5 mg to 15 g, preferably 10 mg to 5 g per liter of the bath of the solution.

In the enzyme determination method of this invention, the synthetic substrate having structure (A) and structure (B) is generally dissolved in a water-containing solvent for practicing an enzyme reaction and in this case if the compound shown by formula (S) below is present in solution in the water-containing medium, the synthetic substrate in the solution is well stabilized, whereby an enzyme measurement method having higher sensitivity can be obtained.

The compound used for stabilization of the dye labelled substances is represented by formula (S) below.

$$D_1\text{-}A\text{-}D_2 \qquad (S)$$

wherein $D_1$ and $D_2$ each represents a condensed polycyclic aromatic heterocyclic moiety or an aromatic heterocyclic ring ring-substituted amino group, which may contain an —$SO_3M$ group, wherein M is a hydrogen atom, an alkali metal or ammonium group, provided that the —A— moiety should contain an —$SO_3M$ group when no —$SO_3M$ group is contained in either $D_1$ or $D_2$ described above.

In formula (S), examples of the condensed polycyclic aromatic heterocyclic residue represented by $D_1$ and $D_2$ include a 2-benzotriazolyl group, a 2-naphthotriazolyl group, etc.; and examples of the aromatic heterocyclic ring-substituted amino group include a 1,3,5-triazin-2-yl amino group, a 1,3-diamin-2-yl amino group, etc.

Preferred examples of the divalent aromatic groups represented by A are as follows:

Sulfo-Containing Groups:

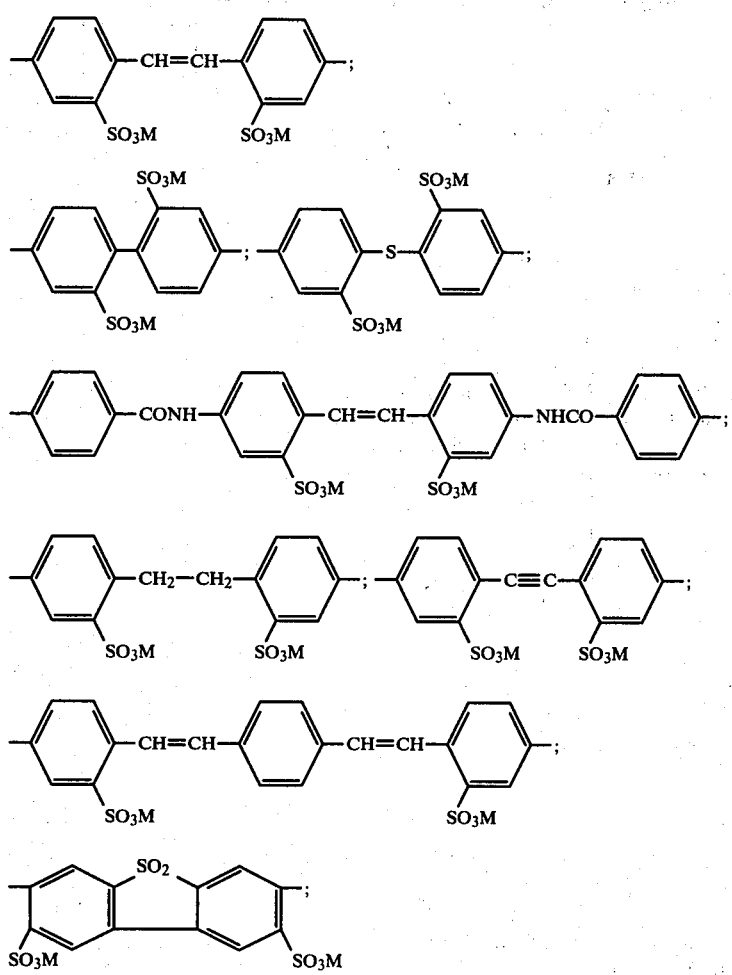

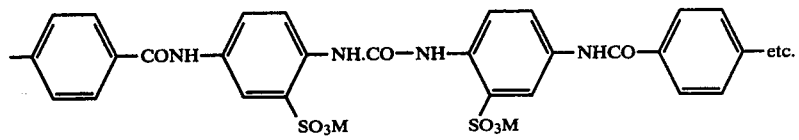

Groups free of a sulfo group:

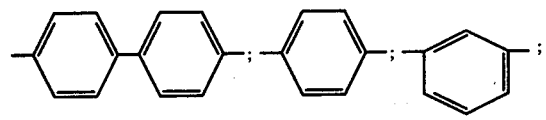

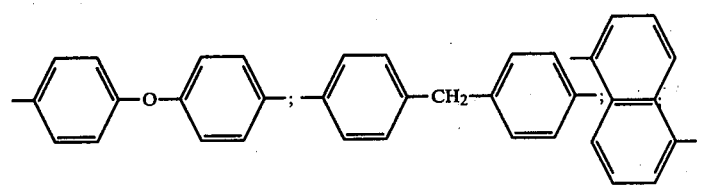

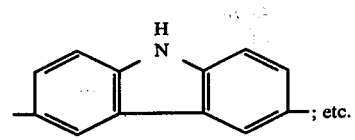

; etc.

When no sulfo group is contained in A, at least one of $D_1$ and $D_2$ contains an —$SO_3M$—containing group.

Of these divalent aromatic residues, more preferred is:

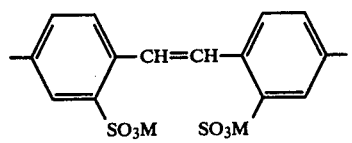

Examples of the alkali metal represented by M include sodium, potassium, etc., and examples of the halogen atom include chlorine, bromine, iodine, etc.

Of compounds represented by formula (S), particularly preferred are those represented by the following formulae (S-I) and (S-II), wherein an alkyl group (including the alkyl moiety contained in an alkoxy group, an alkylthio group, etc. and including a substituent thereon, if any) generally has 1 to 20 carbon atoms, preferably 1 to 12 carbon atoms and an aryl group (including the aryl moiety contain in an aryloxy group, an arylthio group, etc. and including a substituent thereon, if any) generally has 6 to 30 carbon atoms, preferably 6 to 15 carbon atoms, unless otherwise indicated.

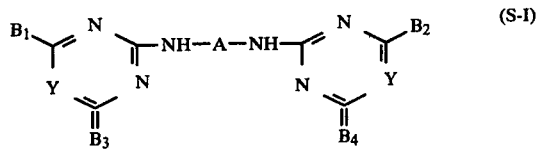

wherein —A— has the same meaning as in formula (S); Y represents =CH—, =$CB_5$— or =N— wherein $B_5$ represents a lower alkyl group, a halogen atom, etc.; $B_1$, $B_2$, $B_3$ and $B_4$ each represents a hydrogen atom, a hydroxy group, an alkoxy group, a lower alkyl group (e.g., a methyl group, an ethyl group, etc.), an aryloxy group (e.g., a phenoxy group, an o-tolyloxy group, a p-sulfophenoxy group), a halogen atom (e.g., a chlorine atom, a bromine atom), a heterocyclic nucleus (e.g., a morpholynyl group, a piperidyl group), an alkylthio group (e.g., a methylthio group, an ethylthio group), a heterocyclylthio group (e.g., a benzothiazolylthio group), an arylthio group (e.g., a phenylthio group, a tolylthio group), an amino group, an alkylamino group or substituted alkylamino group (e.g., a methylamino group, an ethylamino group, a propylamino group, a dimethylamino group, a diethylamino group, a dodecylamino group, a cyclohexylamino group, a β-hydroxyethylamino group, a di(β-hydroxyethyl)amino group, a β-sulfoethylamino group), an arylamino group or substituted arylamino group (e.g., an anilino group, an o-sulfoanilino group, a m-sulfoanilino group, a p-sulfoanilino group, an o-anisylamino group, a m-anisylamino group, a p-anisylamino group, an o-toluidino group, a m-toluidino group, a p-toluidino group, an o-carboxyanilino group, a m-carboxyanilino group, a p-carboxyanilino group, a hydroxyanilino group, a disulfophenylamino group, a naphthylamino group, a sulfonaphthylamino group), a heterocycloamino group (e.g., a 2-benzothiazolylamino group, a 2-pyridylamino group), an aryl group (e.g., a phenyl group), or a mercapto group; $B_1$, $B_2$, $B_3$ and $B_4$ each may be the same or different; when —A— contains no sulfo group, at least one of $B_1$, $B_2$, $B_3$ and $B_4$ should contain at least one sulfo group (which may be a free acid group or form a salt).

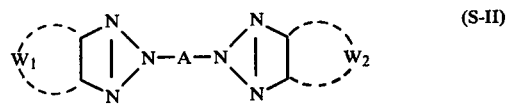

wherein A has the same significance as in formula (S); $W_1$ and $W_2$ each represents the carbon atoms for completing a benzene ring or a naphthalene ring where the benzene ring or naphthalene ring may be substituted and at least one of these substituents, if any, should contain one or more sulfo groups.

For practicing the method of this invention, in a more preferred embodiment, an analysis element used for the method of this invention comprises an auxiliary layer formed under a silver halide-containing layer to increase the amount of spotted test liquid absorbed. The function of the auxiliary layer referred to herein is to accelerate absorption of the spotted test liquid into the layer and increase the uptake of the aforesaid enzyme to be measured, whereby the amount to be adsorbed onto silver halide grains is increased. Such an auxiliary layer is composed of a porous membrane, a filter paper, a fiber, gelatin and/or a polymer and has a thickness of 1 $\mu$m to 100 $\mu$m, preferably 3 $\mu$m to 40 $\mu$m. This auxiliary layer can also contain in addition to gelatin or a polymer, silver halide or additives for ordinary silver halide light sensitive materials, e.g., an antifoggant, a dye, a surface active agent, colloidal silver, etc.

Gelatin, when used in this invention as a binder for silver halide or in other layers, is ordinary lime-treated gelatin, acid-treated gelatin, enzyme-treated gelatin, a gelatin derivative obtained by chemically modifying gelatin, such as phthalated gelatin, or graft gelatin obtained by graft polymerizing a monomer in the presence of gelatin. Such gelatin may be used alone or as a mixture thereof in an appropriate proportion. As polymers used in this invention, polymers which are liable to swell or dissolve in water are preferred, examples of which include albumin, agar agar, gum arabic, alginic acid, a hydrophilic homopolymer or copolymer of a polymerizable vinyl monomer such as vinyl alcohol, vinyl pyrrolidone, acrylamide, acrylic acid, methacrylic acid, styrenesulfonic acid, styrene, methyl methacrylate, etc., a cellulose compound (e.g., hydroxyethyl cellulose, carboxymethyl cellulose, dextrin, etc.), water soluble starch, etc. If necessary or desired, a hardening agent may be added to the polymer to insolubilize the polymer.

The silver halide grains in the silver halide emulsions used in this invention may be ones having an ordinary grain size or ones having a fine grain size, but silver halide grains having a mean grain size or diameter of 0.04 to 4 $\mu$m (measured by, for example, the projected area method) are preferred. Also, the size distribution of the silver halide grains in a silver halide emulsion is preferably as narrow as possible. For this purpose, the silver halide grains may be formed by a double jet method, a conversion method or a controlled double jet method for forming silver halide grains while controlling the pAg of the silver halide grain-forming mixture.

The silver halide emulsion used in this invention may not be chemically ripened but is usually sensitized by conventional chemical sensitization, such as gold sensitization (as described in U.S. Pat. Nos. 2,540,085, 2,597,876, 2,597,915, 2,399,083, etc.), sensitization with metal ions of Group VIII of the Periodic Table, by sulfur sensitization (as disclosed in U.S. Pat. Nos. 1,574,944, 2,278,947, 2,440,206, 2,410,689, 3,189,458 and 3,415,649, etc.), by reduction sensitization (as disclosed in U.S. Pat. Nos. 2,518,698, 2,419,974 and 2,983,610, etc.), or by a combination thereof.

Specific examples of chemical sensitizers include sulfur sensitizers such as allylthio carbamide, thiourea, sodium thiosulfate, cystine, etc.; noble metal sensitizers such as potassium chloroaurate, aurous thiosulfate, potassium chloropalladate, etc.; reduction sensitizers such as stannous chloride, phenylhydrazine, reductone, etc.; polyoxyethylene derivatives as described in British Pat. No. 981,470, Japanese Patent Publication 31-6475 and U.S. Pat. No. 2,716,062, etc.; polyoxypropylene derivatives, quaternary ammonium-containing derivatives, etc.

Silver halide emulsions which are employed in this invention can also contain suitable antifoggants and stabilizers. For example, specific antifoggants and stabilizers include thiazolium salts as described in U.S. Pat. Nos. 2,131,038 and 2,694,716, etc.; azaindenes as described in U.S. Pat. Nos. 2,886,437 and 3,444,605, etc.; urazoles as described in U.S. Pat. No. 3,287,135, etc.; sulfocatechols as described in U.S. Pat. No. 3,236,652, etc.; oximes as described in British Pat. No. 623,448; mercaptotetrazoles as described in U.S. Pat. Nos. 2,403,927, 3,226,897, 3,397,987, etc.; nitron; nitroindazoles; polyvalent metal salts as described in U.S. Pat. No. 2,839,405; thiuronium salts as described in U.S. Pat. No. 3,220,839; and palladium, platinum and gold salts as described in U.S. Pat. No. 2,566,263.

The silver halide emulsions used in this invention may further contain developing agents (e.g., hydroquinones, catechols, aminophenols, 3-pyrazolidones, ascorbic acid and derivatives thereof, reductones, phenylenediamines, etc.), or a combination of these developing agents.

The developing agents can be incorporated in a light sensitive silver halide emulsion layer and/or another suitable layer of the light sensitive analytical element. The developing agent can be added as a solution in a proper solvent or as a form of a dispersion as described in U.S. Pat. No. 2,592,368 and French Pat. No. 1,505,778. When a light sensitive film containing the developing agent in a coated layer or layers is used, the film is processed, after light exposure, with a conventional photographic developer and in this case an alkali activator, i.e., a conventional photographic developer composition from which a developing agent component is removed, may be used.

In this invention, as a binder for the silver halide emulsion layer coated on a support, ordinary gelatin (i.e., alkali-treated gelatin or acid-treated gelatin) is usually used. Furthermore, the gelatin may be partially or wholly replaced with another film-forming high molecular weight material. As such a high molecular weight material, there are used materials which do not have a harmful influence on the light sensitive silver halide emulsion, such as albumin, agar agar, gum arabic, alginic acid, acylated gelatin (e.g., phthalated gelatin, malonated gelatin, etc.), a homopolymer or a hydrophilic vinyl compound (e.g., vinyl alcohol, vinylpyrrolidone, acrylamide, styrenesulfonic acid, acrylic acid, etc.) or copolymers containing these vinyl compounds, cellulose compounds (e.g., hydroxyethyl cellulose, carboxymethyl cellulose, dextrin, etc.), water-soluble starch, etc. Other layers (e.g., a filter layer, subbing layer, etc.) than the silver halide emulsion layer may contain such a film-forming high molecular weight material as in the silver halide emulsion layer.

For exposure of the silver halide having adsorbed thereon the spectrally sensitizing dye constituting a part of the structure of the enzyme reaction product or the unreacted synthetic substrate, various light sources can be used in this invention. However, in all cases, light of the wavelength(s) in the specific absorption wavelength region of the silver halide used is removed and only the light of the wave length(s) adsorbed by the spectrally sensitizing dye is used. For example, a tungsten lamp, a halogen lamp, a mercury lamp, a xenon lamp, etc., is used together with a proper optical filter (e.g., a sharp cut filter made by Fuji Photo Film Co., Ltd., a metal interference filter, etc.,). Also, a solid laser (e.g., ruby laser, etc.,) a semiconductor laser (e.g., lead sulfide laser, etc.), a dye laser, or a gas laser (e.g., neon helium laser, argon laser, etc.), is advantageously used.

The development performed in this invention can be by the following manner. That is, when a silver halide emulsion is formed on a support, a development process as is conventionally used for the development of photographic materials can be used. Also, the photographic development can be performed by spreading, coating, impregnating or spraying a photographic developing composition onto the silver halide emulsion layer formed on the support. Furthermore, when the silver halide emulsion is in the liquid state, photographic development can be performed by mixing the emulsion with a liquid developing composition.

The silver halide emulsion layer contacted with the fogging agent as described above is processed by a conventional photographic processing. A known processing solution can be used in this case. The processing temperature is usually selected from 18° C. to 50° C., but may be lower than 18° C. or higher than 50° C.

With an increase in developing temperature, photographic density increases. Therefore, it is usually preferred to process at a pre-determined constant temperature. However, in place of processing at a constant temperature, a process may be employed wherein changes in photographic density due to changes in developing temperature are substantially prevented by using a neutralizing layer and a temperature compensation polymer layer. For example, the development can be performed on a silver halide emulsion layer formed adjacent a combined layer of an acid polymer layer as described in U.S. Pat. Nos. 3,362,819 and 4,028,103 and a temperature compensation layer as described in U.S. Pat. Nos. 4,056,394 and 4,061,496 and Japanese Patent Application OPI No. 72622/78.

The developer used in the case of performing black and white photographic processing in this invention can contain known developing agents. As such a developing agent, dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and the heterocyclic compounds formed by the condensation of a 1,2,3,4-tetrahydroquinoline ring and an indolene ring as described in U.S. Pat. No. 4,067,872 can be used solely or as a combination of them. The developer may further contain known preservatives, alkali agents, pH buffers, antifoggants, etc., and, if desired or necessary, dissolution aids, color toning agents, development accelerators, surface active agents, defoaming agents, water softeners, hardening agents, tackifiers, etc.

A specific developing process which may be employed is one in which a developing agent is incorporated in a photosensitive material, for example, in the silver halide emulsion layer and the photosensitive material is processed in an aqueous alkali solution. A hydrophobic developing agent may be incorporated in the silver halide emulsion layer as a dispersion in a latex as described in "Research Disclosure", No. 169 as RD-16928. Such a development process using may be combined with a silver salt stabilization process using a thiocyanate.

In place of the above-described black and white development process, a color development as is used in ordinary color photographic process can also be performed. In this case, a coupler is preliminarily dissolved in the developer or incorporated in the silver halide emulsion layer of a photosensitive element (see, for example, T. H. James, "The Theory of the Photographic Process"; 4th Edition, pages 335–362, 1977, published by Macmillan Pub. Co., Inc.).

By color development, areas contacted with the spectral sensitizer gives blackening by silver and coloring by a coloring material, and hence in the color development, a higher optical density than blackening by silver alone is obtained. With developed areas obtained by color development, the light absorption due to blackening of silver and coloring due to dye formation can be measured by light of the light absorption wavelength(s) of the dyes.

After development, a stopping solution may be used in this invention and, as the stopping solution, an aqueous solution containing a compound capable of stopping development such as a pH reducing agent (e.g., a mineral acid, an organic acid, etc.) or a mercapto compound can be used. Also, when the fixing solution used is an acid fixing solution, i.e., having a sufficiently low pH for stopping the development, the stopping solution may be omitted.

As fixing agents, a thiosulfate, a thiocyanate as well as organic sulfur compounds having a fixing effect can be used. The fixing solution may further contain a water-soluble aluminum salt as a hardening agent.

In this invention measurement of photographic density or color density after development can be performed by means of an optical densitometer as is used for measuring the density of conventional photographic images and hence measurement can be performed simply and at a low cost. In the case of measuring optical density, the photographic density or color density can be measured by inserting a proper color filter in the optical path. Usually the photographic density or color density of a photosensitive element which has been finished via conventional photographic processing and dried is measured; however, the photographic density or color density of the photosensitive element immersed in a processing solution may be measured at the end of development, at the end of stopping or at the end of fixing.

Thereafter, this invention will be described in more detail with reference to the examples below.

EXAMPLE 1

In 12.5 ml. of dimethylformamide (DMF) there was dissolved 131 mg. (250 μmoles) of a labelling cyanine dye shown by formula III below:

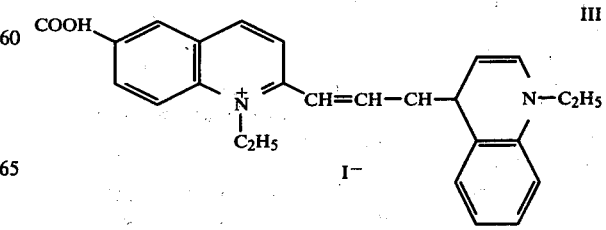

and the solution was cooled to −15° C. To the solution was added 33 μliters (250 μmoles) of isobutyl chloroformate, and after further adding thereto 35 μliters (250 μmoles) of triethylamine, the reaction was performed for 5 minutes at a temperature of −15° C. to −10° C. Then, after further adding 70 mg (250 μmoles) of the acetate of glycylphenylalanylamide and 35 μliters (250 μmoles) of triethylamine to the reaction mixture, reaction was further performed for one hour at 0° C. and then for one further hour at room temperature. To the reaction mixture obtained was added 25 ml of ethyl acetate and the precipitates formed were recovered by filtration and washed with ethyl acetate. The powder thus obtained was repeatedly purified by a silica gel column chromatography (eluate: a 3:1 mixture of chloroform and methanol) and then recrystallized from a 1:1 mixture of chloroform and methanol to provide 128 mg (yield of 71%) of glycylphenylalaninamide the N-terminal of which has been modified or labelled by the dye of formula III.

Melting point: 199°–201° C.

$\lambda_{max}^{MeOH}$ ($\epsilon$)=658 n.m. (1.80×10$^5$).

Mass spectrum (FD) m/z=600 (M-1).

Then, 1 ml of an aqueous solution (0.05 M tris-hydrochloric acid buffer, pH 8.5, and containing 1% of a surface active agent) containing 1 mg/ml of glycylphenylalaninamide labelled with the dye of formula III was mixed with 1 ml. of an aqueous buffer solution containing α-chymotrypsin (made by Sigma Chemicals Inc.) derived from bovine pancreas in an amount of 2 pg/ml, 20 pg/ml or 200 pg/ml and then enzyme reaction was performed in a bath maintained at 40° C. for each of three samples. After 5 mins., 0.1 mg. of tosylamidophenylalanyl chloromethyl ketone—an inactivator for α-chymotrypsin to stop the enzyme reaction—was added and then 1 ml. of each reaction mixture was passed through a small column (4 mm$\phi$×20 mm) packed with carboxymethyl Sephadex C-50 (made by Pharmacia Co., Ltd.) which had been previously activated by the same buffer solution at each concentration of α-chymotrypsin. The column was then washed with 1 ml. of the buffer solution in each case. The effluent and washing (total 2 ml.) were collected at each concentration of α-chymotrypsin. Then, 25 μl of each collected solution was spotted at a diameter of 5 mm on an unexposed silver halide emulsion layer (AgBrCl (70% Br) having a mean grain size of 0.7 μm) formed on a cellulose triacetate film. Also at the same time, the aforesaid substrate diluted two volume times by the buffer and treated by the same procedure as above was spotted side by side by each solution sample as a blank. After 20 mins., each spot was exposed to a flash light of 100 million lux for 10$^{-3}$ seconds through an SC-66 Filter made by Fuji Photo Film Co., Ltd. and then developed by Developer A having the following composition for 5 mins. at 20° C.

| Developer A | |
|---|---|
| Metol | 0.31 g |
| Sodium hydrogen sulfite | 39.6 g |
| Hydroquinone | 6.0 g |
| Sodium carbonate (monohydrate) | 21.9 g |
| Potassium bromide | 0.86 g |
| Citric acid | 0.68 g |
| Potassium metahydrogen sulfite | 1.50 g |

| -continued | |
|---|---|
| Developer A | |
| Water to make | 1 liter |

Each photographic film was then fixed, washed and dried and the photographic density of the photographic film thus obtained was measured by means of a photographic densitometer made by Fuji Photo Film Co., Ltd.

The results obtained are shown in Table 2 below.

TABLE 1

| Density of α-chymotrypsin (pg/ml) | Photographic density |
|---|---|
| 0 | 0.21 |
| 2 | 0.50 |
| 20 | 1.61 |
| 200 | 2.70 |

From the above results, a calibration curve for the determination of α-chymotrypsin could be obtained in a wide concentration range.

EXAMPLE 2

The same procedure as in Example 1 was followed using the same materials and the same concentration (1 mg/ml) of the substrate solution except that each of the concentrations of the enzyme solutions were increased 10 times, i.e., to 20 pg/ml, 200 pg/ml, and 2,000 pg/ml and also an ND filter of an optical density of 1.0 was placed in front of the light source. The results obtained are shown in following Table 2.

TABLE 2

| Concentration of α-chymotrypsin (pg/ml) | Photographic density |
|---|---|
| 0 | 0.08 |
| 20 | 0.39 |
| 200 | 1.50 |
| 2000 | 2.61 |

From the above results, a calibration curve for the determination of α-chymotrypsin could be obtained in a wider concentration range than that in Example 1.

On comparing the results with those of Example 1, the results show that the measuring concentration range can be sufficiently controlled by exposure conditions in the method of this invention.

EXAMPLE 3

Using the glycylphenylalaninamide labelled by the dye of formula III obtained in Example 1 as the synthetic substrate, the amount of α-chymotrypsin contained in commercially available crude trypsin was determined.

The activity of α-chymotrypsin in each sample was measured under the same conditions as in Example 1 except that buffer solutions containing 100 pg, 1 ng, or 10 ng of commercially available trypsin (crude product) per milliliter of the buffer solution were used and 0.1 mg of an inactivator for trypsin, tosylamidolysylchloromethyl ketone was used.

The results obtained are shown in Table 3 below.

TABLE 3

| Concentration of trypsin (ng/ml) | Photographic density |
|---|---|
| 0 | 0.19 |

TABLE 3-continued

| Concentration of trypsin (ng/ml) | Photographic density |
|---|---|
| 0.1 | 0.45 |
| 1.0 | 1.35 |
| 10.0 | 1.95 |

By calibrating the results shown above from the results of Table 1 in Example 1, it was found that 1.5% α-chymotrypsin (calculated as α-chymotrypsin in Example 1) was contained in the trypsin.

EXAMPLE 4

By following the same procedure as in Example 1 using 68 mg (250 μmoles) of 4-aminophenyl-β-D-galactopyranoside obtained by catalytically reducing commercially available 4-nitrophenyl-β-D-galactopyranoside in place of glycylphenylalaninamide in Example 1, the synthetic substrate of following formula (I) was prepared.

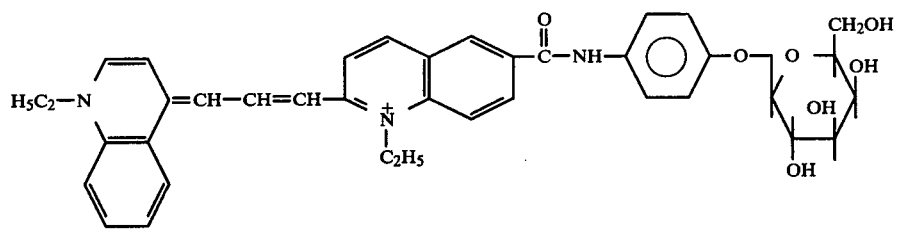

Formula (I)

The crude crystals obtained were purified by reprecipitating with a DMF-ethyl acetate solvent system and further recrystallizing from a mixture of methanol and chloroform (1:1 by volume ratio). The amount of the product obtained was 132 mg (yield of 68%).

Melting point: 269°–272° C.
Mass spectrum (FD) m/e=651 (M-1).
$\lambda_{max}^{MeOH}$ (ε)=658 (1.81×10$^5$).

It was confirmed by TLC and ultraviolet and visible absorption spectra that the compound was hydrolyzed by β-D-galactosidase (made by Sigma Co.) to release the compound of following formula (II):

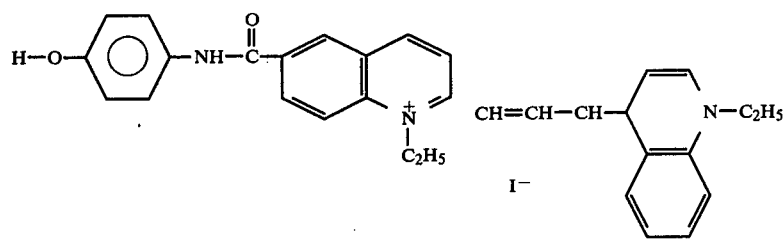

(II)

Then, an IgG-β-D-galactosidase complex was prepared using β-D-galactosidase derived from E. coli and anti α-fetoprotein rabbit IgG with N,N'-o-phenylenedimaleimide. Also, an anti α-fetoprotein antibody-insolubilizing glass bead immobilized with anti α-fetoprotein rabbit antibody was prepared using glass beads having introduced an amino group and glutaraldehyde (details are given in Eiji Ishikawa, ENZYME IMMUNOASSAY, published by Igaku Shoin, 1978).

A calibration curve of a standard α-fetoprotein solution was prepared by the following method using above anti α-fetoprotein rabbit IgG-β-D-galactosidase, anti α-fetoprotein rabbit IgG-insolubilizing glass beads (simply glass beads) and the compound of aforesaid formula (II).

To a test tube containing 0.4 ml. of a 0.1 M sodium phosphate buffer solution of pH 7.3 (solution A) containing 0.15 M NaCl and 0.5% bovine serum albumin (BSA) were added 0.1 ml. of each standard α-fetoprotein (5 to 160 ng/ml) solution of each concentration prepared using solution A and 20 liters of horse serum. Then, to each test tube was added one glass bead whereby the antibody was insolubilized as described above and then the test tube was allowed to stand for 2 hrs. at 37° C. Then, the reaction solution was suctioned using an aspirator and the residual glass bead was washed twice with 1 ml. each of a 0.01 M sodium phosphate buffer solution of pH 7.5 (solution B) containing 0.1 M NaCl, 1 mM MgCl$_2$, and 0.1% BSA. After washing 0.2 ml. each of an anti α-fetoprotein antibody-β-D-galactosidase conjugate diluted in solution B was added to the glass bead and the mixture was allowed to stand for 2 hrs. at 37° C. The dilution magnitude of the conjugate was selected so that the photographic density after the following development was 2.0 to 2.5. 160 ng/ml of standard α-fetoprotein of the reaction mixture was decanted and the glass bead was washed twice with 1 ml. each of solution B.

Then, the glass bead was immersed in 0.5 ml. each of a solution of 0.1% of the compound of formula (I) dissolved in solution B and allowed to stand for 20 mins. at 37° C. The reaction product (compound of formula II) was separated from each reaction mixture by means of a silica gel column 3 mmφ×15 mm (using a solvent system of chloroform and methanol) and, after distilling off the solvent, the residue was dissolved in 0.2 ml. of solution B. Thereafter, the product was measured by a light sensitive film having a silver halide emulsion layer as in Example 1.

The photographic density of each standard solution thus obtained is shown in Table 4.

TABLE 4

| Concentration of standard solution (ng/ml) | Photographic density |
|---|---|
| 0 | 0.18 |
| 2.5 | 0.14 |

TABLE 4-continued

| Concentration of standard solution (ng/ml) | Photographic density |
|---|---|
| 5 | 0.71 |
| 10 | 0.98 |
| 20 | 0.31 |
| 40 | 1.62 |
| 80 | 1.90 |
| 160 | 2.19 |

As is clear from the above results, the determination of the desired component could be performed in a trace concentration range by the method of this invention.

While the invention has been described in detail and with reference to specific embodiments thereof, it will be apparent from one skilled in the art that various changes and modifications can be made therein without departing from the spirit and scope thereof.

What is claimed is:

1. A method for determining the activity and/or amount of a particular enzyme in a sample comprising:
   (a) providing a synthetic substrate comprising at least one structure (A) catalytically affected by the enzyme being assayed and at least one spectrally sensitizing dye structure (B), said structures (A) and (B) being found in the molecular structure of the synthetic substrate;
   (b) contacting the sample with the provided synthetic substrate so as to bring about a chemical reaction by said enzyme;
   (c) contacting either the reaction product resulting from (b) or the excess unreacted synthetic substrate also resulting from (b) with silver halide;
   (d) exposing the silver halide of either product resulting from (c) to light having wavelengths corresponding to the absorption spectra of the spectrally sensitizing dye structures (B);
   (e) photographically developing the silver halide-treated product resulting from (d) with either a black-and-white or color development process; and
   (f) measuring the optical density of the developed silver and/or colored dye resulting from (e).

2. The method as claimed in claim 1 wherein said enzyme is a proteolytic enzyme, a peptide-decomposing enzyme, a nucleic acid-decomposing enzyme, a glycoside-decomposition enzyme, or a lipid-decomposing enzyme.

3. The method as claimed in claim 1 wherein the enzyme is a proteolytic-enzyme, a nucleic acid-decomposing enzyme, a glucoside-decomposing enzyme or a lipid-decomposition enzyme, and the synthetic substrate is linked to an insoluble carrier.

4. The method as claimed in claim 1 wherein the enzyme is a proteolytic enzyme, a nucleic acid-decomposition enzyme, a glucoside-decomposing enzyme or a lipid-decomposing enzyme and the synthetic substrate comprises at least two structure (A)s and at least two structure (B)s.

5. The method as claimed in claim 1 wherein two or more enzymes are reacted with a number of synthetic substrates the same as the number of enzymes, each synthetic substrate having a different structure (A) specifically corresponding to each enzyme and each different spectrally sensitizing dye structure (B) having different spectrally sensitizing wavelength region(s), either the reaction the reaction product having each different structure (B) formed by the enzyme reaction or the unreacted synthetic substrate being brought into contact with a silver halide, the silver halide being exposed to light having a spectrally sensitizing wavelength region corresponding to each different sensitizing dye structure (B) of each synthetic substrate for each enzyme followed by development, and then each enzyme activity and/or each enzyme amount is measured from the optical density of developed silver and/or colored dye corresponding to each exposed portion.

6. The method of claim 1 wherein a plurality of enzyme activities in a system containing at least two enzymes are determined individually in a scheme involving selectively inhibiting or inactivating individual enzymes on at a time.

7. The method as claimed in claim 1 wherein the enzyme is an enzyme labeling an antigen or antibody.

8. The method as claimed in claim 1 wherein either the enzyme reaction product having structure (B) or the unreacted synthetic substrate is brought into contact with the silver halide in the presence of a hydrazine compound of the following general formula, the silver halide is exposed to light of the spectrally sensitizing wavelength(s) corresponding to the sensitizing dye structure (B), and then developed:

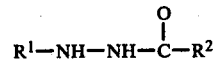

wherein $R^1$ represents a substituted or unsubstituted aryl group and $R^2$ represents a hydrogen atom, a substituted or unsubstituted alkyl group, or a substituted or unsubstituted aryl group.

9. The method as in claim 1 wherein the silver halide is in a form of a light sensitive silver halide emulsion layer formed on a support and contact of the enzyme reaction mixture or the unreacted synthetic substrate is performed by spotting it on the silver halide emulsion layer.

10. The method as claimed in claim 9 wherein the light sensitive silver halide emulsion contains a coupler and development of the emulsion layer after light exposure is a color development.

* * * * *